United States Patent

Stemp et al.

[11] Patent Number: 6,008,219
[45] Date of Patent: Dec. 28, 1999

[54] BICYCLIC AMINE DERIVATIVES AND THEIR USE AS ANTI-PSYCHOTIC AGENTS

[75] Inventors: Geoffrey Stemp, Bishop's Stortford; Christopher Norbert Johnson, Saffron Walden, both of United Kingdom

[73] Assignee: SmithKline Beech p.l.c., Brentford, United Kingdom

[21] Appl. No.: 08/913,919

[22] PCT Filed: Mar. 21, 1996

[86] PCT No.: PCT/EP96/01238

§ 371 Date: Oct. 29, 1997

§ 102(e) Date: Oct. 29, 1997

[87] PCT Pub. No.: WO96/30333

PCT Pub. Date: Oct. 3, 1996

[30] Foreign Application Priority Data

Mar. 27, 1995 [GB] United Kingdom .................... 9506169
Sep. 12, 1995 [GB] United Kingdom .................... 9518573
Dec. 13, 1995 [GB] United Kingdom .................... 9525480

[51] Int. Cl.$^6$ ..................... A61K 31/165; A61K 31/35; A61K 31/38; A61K 31/44; A61K 31/505; A61K 31/41; C07D 271/06; C07D 285/06; C07D 311/58; C07D 335/06; C07D 233/78

[52] U.S. Cl. ..................... 514/241; 514/242; 514/247; 514/256; 514/357; 514/359; 514/361; 514/362; 514/363; 514/364; 514/365; 514/372; 514/374; 514/378; 514/383; 514/399; 514/427; 514/438; 514/471; 514/253; 514/337; 514/397; 514/422; 514/432; 514/459; 514/617; 514/618; 514/619; 514/621; 514/622; 544/180; 544/182; 544/224; 544/335; 544/238; 544/333; 546/330; 546/335; 546/280.1; 546/282.7; 546/283.1; 548/127; 548/128; 548/131; 548/134; 548/136; 548/143; 548/187; 548/214; 548/236; 548/247; 548/255; 548/267.6; 548/338.1; 548/561; 548/256; 548/266.4; 548/311.4; 548/525; 549/77; 549/496; 549/23; 549/396; 549/162; 549/163; 549/168; 549/169; 549/170; 549/171; 549/172; 549/174; 549/176; 549/180; 549/185

[58] Field of Search ..................... 548/127, 128, 548/131, 134, 136, 143, 187, 214, 236, 256, 267.6; 546/330, 335; 544/335, 180, 224, 182; 564/169, 168, 176, 180, 170, 185, 171, 162, 172, 174; 514/361, 362, 364, 363, 357, 365, 256, 247, 399, 359, 242, 383, 372, 374, 378, 617, 618, 427, 621, 619, 438, 471, 622

[56] References Cited

U.S. PATENT DOCUMENTS 4,410,519 10/1983 Seiler et al. ............................ 424/226
4,880,802 11/1989 Schohe et al. ....................... 514/222.2
5,118,704 6/1992 Minaskanian et al. ................. 514/416

FOREIGN PATENT DOCUMENTS 0 026 848 4/1981 European Pat. Off. .
0 064 964 11/1982 European Pat. Off. .
0 270 947 6/1988 European Pat. Off. .
0 666 250 8/1995 European Pat. Off. .
WO 95/04039 2/1995 WIPO .

OTHER PUBLICATIONS

Boyfield et al., "A Novel Series of 2–Aminotetralins with High Affinity and Selectivity for the Dopamine D3 Receptor," Bioorganic & Medicinal Chemistry Letters, vol. 7, No. 15, pp. 1995–1998, 1997.

*Primary Examiner*—John M. Ford
*Assistant Examiner*—Ann M. Kessinger
*Attorney, Agent, or Firm*—Nora Stein-Fernandez; Janice E. Williams; Charles M. Kinzig

[57] ABSTRACT

This invention relates to compounds of formula (I)

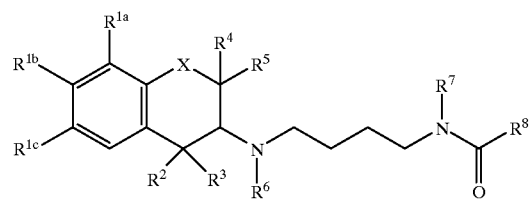

which are useful as modulators of $D_3$ receptors, in particular as antipsychotic agents.

11 Claims, No Drawings

BICYCLIC AMINE DERIVATIVES AND THEIR USE AS ANTI-PSYCHOTIC AGENTS

This application is a 371 of PCT/EP96/01238 filed Mar. 21, 1996.

The present invention relates to novel amino-substituted bicyclic derivatives, processes for their preparation, pharmaceutical compositions containing them and their use in therapy, as modulators of $D_3$ receptors, in particular as antipsychotic agents.

European Patent Application No. 26848, describes a class of 2-amino-5-hydroxy-1,2,3,4-tetrahydronaphthalenes which are said to be inhibitors of prolactin secretion and to be useful in the treatment of circulatory disorders and Parkinsonism.

European Patent Application No. 270947 describes compounds of the formula:

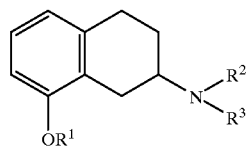

wherein $R^1$ is hydrogen or alkyl; $R^2$ is inter alia alkyl; $R^3$ is inter alia a group —$(CH_2)_aR^4$ wherein a is from 1 to 10 and $R^4$ may be —$NR^{11}R^{12}$. The meanings of $R^{11}$ and $R^{12}$ may be selected from inter alia hydrogen and $COR^{13}$ and $R^{13}$ may be inter alia aryl having 6–12 carbon atoms, e.g. phenyl, naphthyl or biphenyl. These compounds are said to have affinity for cerebral receptors of the 5-$HT_1$ type and to be useful in the treatment of a variety of conditions including anxiety, depression, cognitive deficits and migraine.

We have now found a class of amino-tetralin derivatives which have affinity for dopamine receptors, in particular the $D_3$ receptor, and thus potential in the treatment of conditions wherein modulation of the $D_3$ receptor is beneficial, eg as antipsychotic agents.

In a first aspect the present invention provides compounds of formula (I):

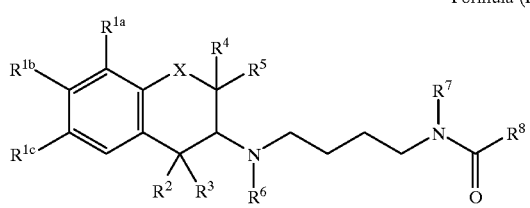

Formula (I)

wherein

X represents a single bond, O, S or $CR^9R^{10}$ where $R^9$ and $R^{10}$ each independently represent a hydrogen atom or a $C_{1-4}$alkyl group;

$R^{1a}$, $R^{1b}$ and $R^{1c}$ each independently represent a substituent selected from: a hydrogen or halogen atom, a hydroxy, cyano, trifluoromethyl, trifluoromethoxy, trifluoromethanesulfonyloxy, $C_{1-4}$alkyl, $C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy or arylsulphonyl$C_{1-4}$alkyl group or a group $R^{11}OCO(CH2)_p$, $R^{11}R^{12}NCO(CH2)_p$ or $R^{11}R^{12}NSO_2(CH_2)_p$ where each of $R^{11}$ $R^{12}$ independently represents a hydrogen atom or a $C_{1-4}$alkyl group and p represents zero or an integer from 1 to 4;

$R^2$, $R^3$, $R^4$ and $R^5$ each independently represent a hydrogen atom or a $C_{1-4}$alkyl group;

$R^6$ represents a hydrogen atom or a $C_{1-6}$alkyl, $C_{3-6}$alkenyl or aryl$C_{1-4}$alkyl group;

$R^7$ represents a hydrogen atom or a $C_{1-4}$alkyl group; and $R^8$ represents a group of structure (a), (b) or (c):

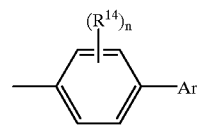

(a)

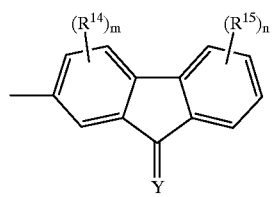

(b)

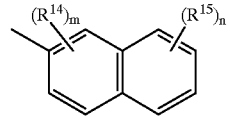

(c)

wherein

Ar represents an optionally substituted 5- or 6-membered aromatic heterocyclic ring or a group of structure (d):

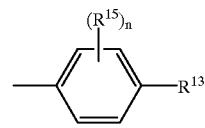

(d)

$R^{13}$ represents a hydrogen or halogen atom, or a hydroxy, cyano, nitro, $H_2NCO$, $C_{1-4}$alkyl, $C_{1-4}$alkoxy, $C_{1-4}$alkanoyl or $C_{1-4}$alkylsulphonyl group or an optionally substituted 5- or 6-membered heterocyclic ring;

each $R^{14}$ and $R^{15}$ independently represents a substituent selected from: a hydrogen or halogen atom, or a hydroxy, cyano, nitro, $H_2NCO$, $C_{1-4}$alkyl, $C_{1-4}$alkoxy $C_{1-4}$alkanoyl or $C_{1-4}$alkylsulphonyl, group;

Y represents $H_2$ or an oxygen atom;

n is a number from 1 to 4; and m is a number from 1 to 3;

and salts thereof.

In the compounds of formula (I) above an alkyl or alkenyl group or moiety may be straight or branched. Alkyl groups which may be employed include methyl, ethyl, n-propyl, n-butyl, n-pentyl, n-hexyl and any branched isomers thereof such as isopropyl, t-butyl, sec-pentyl, and the like. Alkenyl groups may similarly be straight or branched. Further the double bond may be at any appropriate position in the alkenyl chain.

When one or more of $R^{1a}$, $R^{1b}$ and $R^{1c}$ represents an arylsulphonyl, arylsulphonyloxy or arylsulphonyl$C_{1-4}$alkyl group, the aryl moiety may be selected from phenyl, naphthyl, and tetrahydronaphthyl; preferably the aryl moiety is phenyl.

A halogen atom present in the compounds of formula (I) may be fluorine, chlorine, bromine or iodine.

$R^{1a}$, $R^{1b}$ and $R^{1c}$ preferably each independently represent a hydrogen or halogen (eg fluorine, chlorine or bromine) atom, or a hydroxy, cyano, trifluoromethoxy, trifluoromethanesulfonyloxy, $C_{1-4}$alkoxy (eg methoxy), $C_{3-6}$cycloalkyl$C_{1-4}$alkoxy (eg cyclopropylmethoxy), $C_{1-4}$alkylsulphonyl (eg methanesulphonyl), $C_{1-4}$alkylsulphonyloxy (eg methanesulphonyloxy), $C_{1-4}$alkylsulphonyl$C_{1-4}$alkyl (eg methanesulphonylmethyl), $C_{1-4}$alkylthio, $R^{11}OCO(CH_2)p$ (eg a carboxyl group or alkyl ester thereof such as COOEt) or $R^{11}R^{12}NCO(CH2)_p$ (eg carboxamido, N-methylcarboxamido or N,N-dimethylcarboxamido), group.

In one embodiment $R^{1a}$, $R^{1b}$ and $R^{1c}$ preferably independently represent hydrogen, hydroxy, cyano, or $H_2NCO$. In a further embodiment $R^{1a}$, $R^{1b}$ and $R^{1c}$ preferably independently represent hydrogen, halogen, trifluoromethyl, trifluoromethoxy, $C_{1-4}$alkylsulphonyloxy, trifluoromethanesulphonyloxy, or $R^{11}OCO(CH_2)p$.

Advantageously, one of $R^{1a}$, $R^{1b}$ and $R^{1c}$ is a group other than hydrogen and the other two of $R^{1a}$, $R^{1b}$ and $R^{1c}$ are each hydrogen.

X preferably represents oxygen, a single bond, or —$CR^9R^{10}$; $R^9$ and $R^{10}$ are suitably both hydrogen.

$R^2$ and $R^3$ preferably each represent hydrogen or $C_{1-2}$alkyl (eg methyl).

$R^4$ and $R^5$ preferably each represent hydrogen.

$R^6$ preferably represents methyl, ethyl, propyl or propenyl.

$R^7$ preferably represents a hydrogen atom.

In any of the groups (a) (b) or (c) represented by the substituent $R^8$, or in the group (d) when n or m represents a number greater than 1 the substituents on the ring in question may be the same or different; e.g. when $(R^{14})_n$ in the group (a) represents two or more substituents each $R^{14}$ may be the same or different and may also be the same as or different from any substituent $R^{15}$ present in group (a). $R^8$ preferably represents a group (a).

In the group (a) when Ar represents an optionally substituted 5- or 6-membered heterocyclic aromatic ring or in the group (d) when $R^{13}$ represents an optionally substituted 5-membered heterocyclic ring, said ring may contain from 1 to 4 heteroatoms selected from O, N or S. When the ring contains 2–4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl. Optional substituents may be selected from those listed above for $R^{14}$ and $R^{15}$. Preferred aromatic heterocyclic groups for Ar include thiadiazolyl, pyrimidinyl and pyridyl.

When Ar represents a group (d) $R^{13}$ preferably represents a hydrogen atom, a $C_{1-4}$alkoxy (eg methoxy), $C_{1-4}$alkanoyl (eg acetyl) or $C_{1-4}$alkylsulphonyl (eg methanesulfonyl) group or an optionally substituted 5-membered heterocyclic group (eg. selected from the 5-membered aromatic heterocyclic groups defined above, such as 5-methyl-1,2,4-oxadiazolyl).

$R^{14}$ in the group (a) and $R^{15}$ in the group (d) preferably each independently represent hydrogen or $C_{1-4}$ alkyl (eg methyl). When either of $R^{14}$ or $R^{15}$ is other than hydrogen, n is preferably 1.

When $R^8$ represents a group (b) $R^{14}$ and $R^{15}$ preferably each represent hydrogen. Y preferably represents O.

When $R^8$ represents a group (c) $R^{14}$ and $R^{15}$ preferably each represent hydrogen.

A particular class of compounds of formula (I) comprises those wherein:

X, $R^2$, $R^3$, $R^4$, $R^5$, $R^6$ and $R^7$ are as defined for formula (I) above;

$R^{1a}$ and $R^{1c}$ each independently represent a substituent selected from: a hydrogen atom, a hydroxy, $C_{1-4}$alkoxy, $C_{1-4}$alkanoyl, $C_{1-4}$alkoxycarbonyl, or trifluoromethanesulfonyloxy group, or a group $R^{11}R^{12}NCO$ where each of $R^{11}$ and $R^{12}$ independently represents a hydrogen atom or a $C_{1-4}$alkyl group;

$R^{1b}$ represents a hydrogen atom;

$R^8$ represents a group of structure (a) in which Ar represents a group of structure (d) wherein $R^{13}$ represents a hydrogen atom, a $C_{1-4}$alkanoyl or $C_{1-4}$alkyl group or $R^{13}$ is a group of the structure:

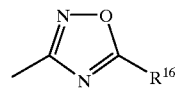

wherein $R^{16}$ represents a hydrogen atom or a $C_{1-4}$alkyl group;

or $R^8$ represents a group (b) or (c) as defined for formula (I) above;

each $R^{14}$ and $R^{15}$ independently represents a substituent selected from: a hydrogen or halogen atom, or a $C_{1-4}$alkyl, $C_{1-4}$alkoxy, hydroxy, cyano or nitro, group;

Y represents $H_2$ or an oxygen atom;

n is a number from 1 to 4; and m is a number from 1 to 3;

and salts thereof.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulphuric, nitric or phosphoric acid; and organic acids eg. succinic, maleic, acetic, fumaric, citric, tartaric, benzoic, p-toluenesulphonic, methanesulphonic or naphthalenesulphonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

When an asymmetric centre is present in a compound of formula (I) the compound will exist in the form of optical isomers (enantiomers). The present invention includes within its scope all such enantiomers and mixtures, including racemic mixtures, thereof. In addition, all possible diastereomeric forms (individual diastereomers and mixtures thereof) of compounds of formula (I) are included within the scope of the invention. When the compound of formula (I) contains an alkenyl group or moiety, geometric isomers may arise and these are likewise within the scope of the present invention.

Particular compounds according to the invention include:

N-(4-(4-phenylbenzoylamino)butyl)-2-(R,S)-methylamino-1,2,3,4-tetrahydronaphthalene;

5-methoxy-N-(4-(4-phenylbenzoylamino)butyl)-2-(R,S)-methyl-amino-1,2,3,4-tetrahydronaphthalene;

5-hydroxy-N-(4-(4-phenylbenzoylamino)butyl)-2-(R,S)-methylamino-1,2,3,4-tetrahydronaphthalene;

7-Methoxy-N-(4-(4-phenylbenzoylamino)butyl)-2-(R,S)-methylamino-1,2,3,4-tetrahydronaphthalene, 7-Hydroxy-N-(4-(4-phenylbenzoylamino)butyl)-2-(R,S)-methylamino-1,2,3,4-tetrahydronaphthalene,
5-Methoxy-N-(4-(4-phenylbenzoylamino)butyl)-2-(R,S)-propylamino-1,2,3,4-tetrahydronaphthalene,
8-Methoxy-N-(4-(4-phenylbenzoylamino)butyl)-3-(R,S)-methylamino-3,4-dihydro-2H-benzo[b]pyran,
6-Methoxy-N-(4-(4-phenylbenzoylamino)butyl)-2-(R,S)-methylamino-1,2,3,4-tetrahydronaphthalene,
6-Methoxy-N-(4-(4-phenylbenzoylamino)butyl)-3-(R,S)-methylamino-3,4-dihydro-2H-benzo[b]pyran,
8-Methoxy-N-(4-(4-phenylbenzoylamino)butyl)-3-(R,S)-propylamino-3,4-dihydro-2H-benzo[b]pyran,
5-Methoxy-N-(4-(4-phenylbenzoylamino)butyl)-2-(R,S)-ethylamino-1,2,3,4-tetrahydronaphthalene,
7-Methoxy-N-(4-(4-phenylbenzoylamino)butyl)-2-(R,S)-propylamino-1,2,3,4-tetrahydronaphthalene,
N-(4-(4-Phenylbenzoylamino)butyl)-3-(R,S)-propylamino-3,4-dihydro-2H-benzo[b]pyran,
N-(4-(4-Phenylbenzoylamino)butyl)-3-(R,S)-methylamino-3,4-dihydro-2H-benzo[b]pyran,
7-Hydroxy-N-(4-(2-methyl-4-phenyl)benzoylamino)butyl-2-(R,S)-methylamino-1,2,3,4-tetrahydronaphthalene,
7-Hydroxy-N-(4-(3-methyl-4-phenyl)benzoylamino)butyl-2-(R,S)-methylamino-1,2,3,4-tetrahydronaphthalene,
7-Hydroxy-N-(4-(4-(1,2,3-thiadiazolyl))benzoyl-amino)butyl)-2-(R,S)-methylamino-1,2,3,4-tetrahydronaphthalene,
7-Hydroxy-N-(4-(4-(4-acetyl)phenyl)benzoylamino)butyl-2-(R,S)-methylamino-1,2,3,4-tetrahydronaphthalene,
7-Hydroxy-N-(4-(2-naphthoyl)amino)butyl-2-(R,S)-methylamino-1,2,3,4-tetrahydronaphthalene,
6-Hydroxy-N-(4-(4-phenlbenzoylamino)butyl)-3-(R,S)-methylamino-3,4-dihydro-2H-benzo[b]pyran,
7-Hydroxy-N-(4-(4-(4-methanesulfonyl)phenyl)benzoyl-amino)butyl-2-(R,S)-methylamino-1,2,3,4-tetrahydronaphthalene,
7-Hydroxy-N-(4-(4-(4-(3-(5-methyl-(1,2,4-oxadiazolyl)))-2-methylphenyl)benzoylamino)butyl)-2-(R,S)-methylamino-1,2,3,4-tetrahydronaphthalene,
5-Hydroxy-N-(4-(4-phenylbenzoylamino)butyl)-2-(R,S)-propylamino-1,2,3,4-tetrahydronaphthalene,
(R or S)-5-Methoxy-N-(4-(4-phenylbenzoylamino)butyl)-2-methylamino-1,2,3,4-tetrahydronaphthalene, (Enantiomer A),
(R or S)-5-Hydroxy-N-(4-(4-phenylbenzoylamino)butyl)-2-methylamino-1,2,3,4-tetrahydronaphthalene, (Enantiomer A),
(R or S)-5-Methoxy-N-(4-(4-phenylbenzoylamino)butyl)-2-methylamino-1,2,3,4-tetrahydronaphthalene, (Enantiomer B),
(R or S)-5-Hydroxy-N-(4-(4-phenylbenzoylamino)butyl)-2-methylamino-1,2,3,4-tetrahydronaphthalene, Enantiomer B),
2-(4-(4-Phenylbenzoylamino)butylaminoindane,
N-(4-(4-Phenylbenzoylamino)butyl)-2-methylaminoindane,
7-Methoxy-N-(4-(2-(9-oxofluorenyl))carboxamido)butyl-2-(R,S)-methylamino-1,2,3,4-tetrahydronaphthalene,
7-Methoxy-N-(4-(3-methyl-4-phenyl)benzoylamino)butyl-2-(R,S)-methylamino-1,2,3,4-tetrahydronaphthalene,
7-Methoxy-N-(4-(2-methyl-4-phenyl)benzoylamino)butyl-2-(R,S)-methylamino-1,2,3,4-tetrahydronaphthalene,
7-Methoxy-N-(4-(4-(4-(1,2,3-thiadiazolyl))benzoylamino)-butyl)-2-(R,S)-methylamino-1,2,3,4-tetrahydronaphthalene,
7-Methoxy-N-(4-(4-(4-acetyl)phenyl)benzoylamino)butyl-2-(R,S)-methylamino-1,2,3,4-tetrahydronaphthalene,
7-Methoxy-N-(4-(4-(4-(3-(5-methyl-(1,2,4-oxadiazolyl)))-2-methylphenyl)benzoylamino)-2-(R,S)-methylamino-1,2,3,4-tetrahydronaphthalene,
N-(4-(4-phenylbenzoylamino)butyl)-2-(R,S)-propylamino-1,2,3,4-tetrahydronaphthalene,
7-Methoxy-N-(4-(2-naphthoyl)amino)butyl-2-(R,S)-methyl-amino-1,2,3,4-tetrahydronaphthalene,
7-Hydroxy-N-(4-(4-(4-methoxy)phenyl)benzoylamino)butyl-2-(R,S)-methylamino-1,2,3,4-tetrahydronaphthalene,
7-Hydroxy-N-(4-(4-(4-pyridyl)benzoyl)amino)butyl-2-(R,S)-methylamino-1,2,3,4-tetrahydronaphthalene,
7-Hydroxy-N-(4-(4-(3-pyridyl)benzoyl)amino)butyl-2-(R,S)-methylamino-1,2,3,4-tetrahydronaphthalene,
7-Hydroxy-N-(4-(4-(2-pyridyl)benzoyl)amino)butyl-2-(R,S)-methylamino-1,2,3,4-tetrahydronaphthalene,
7-Hydroxy-N-(4-(2-(9-oxofluorenyl))carboxamido)butyl-2-(R,S)-methylamino-1,2,3,4-tetrahydronaphthalene,
7-Methoxy-N-(4-(4-(4-methansulfonyl)phenyl)benzoyl-amino)butyl-2-(R,S)-methylamino-1,2,3,4-tetrahydronaphthalene,
N-(4-(4-Phenylbenzoylamino)butyl)-2-(R,S)-propylamino-5-trifluoromethanesulfonyloxy-1,2,3,4-tetrahydronaphthalene,
5-Cyclopropylmethoxy-N-(4-(4-phenylbenzoylamino)butyl)-2-(R,S)-propylamino-1,2,3,4-tetrahydronaphthalene,
5-Chloro-N-(4-(4-phenylbenzoylamino)butyl)-2-(R,S)-propylamino-1,2,3,4-tetrahydronaphthalene,
6-Fluoro-N-(4-(4-phenylbenzoylamino)butyl)-2-(R,S)-propylamino-1,2,3,4-tetrahydronaphthalene,
7-Chloro-N-(4-(4-phenylbenzoylamino)butyl)-2-(R,S)-propylamino-1,2,3,4-tetrahydronaphthalene,
6-Chloro-N-(4-(4-phenylbenzoylamino)butyl)-2-(R,S)-propylamino-1,2,3,4-tetrahydronaphthalene,
6-Bromo-N-(4-(4-phenylbenzoylamino)butyl)-2-(R,S)-propylamino-1,2,3,4-tetrahydronaphthalene
N-(4-(4-(4-Pyridyl)benzoyl)amino)butyl-2-(R,S)-propylamino-1,2,3,4-tetrahydronaphthalene,
8-Hydroxy-N-(4-(4-phenylbenzoylamino)butyl)-3-(R,S)-propylamino-3,4-dihydro-2H-benzopyran,
N-(4-(4-Phenylbenzoylamino)butyl)-3-(R,S)-propylamino-8-trifluoromethanesulfonyloxy-3,4-dihydro-2H-benzopyran,
N-(4-(4-Phenylbenzoylamino)butyl)-2-propylaminoindane,
N-(4-(4-Phenylbenzoylamino)butyl-2-(2-propenyl)aminoindane,
cis-5-Methoxy-1-methyl-N-(4-(4-phenylbenzoylamino)butyl)-2-(R,S)-propylamino-1,2,3,4-tetrahydronaphthalene,
N-(4-(4-Phenylbenzoylamino)butyl)-2-(R,S)-propylamino-5-trifluoromethoxy-1,2,3,4-tetrahydronaphthalene,
6-Methylthio-N-(4-(4-phenylbenzoylamino)butyl)-2-(R,S)-propylamino-1,2,3,4-tetrahydronaphthalene,
5-Fluoro-N-(4-(4-phenylbenzoylamino)butyl)-2-(R,S)-propylamino-1,2,3,4-tetrahydronaphthalene,
7-Methylthio-N-(4-(4-phenylbenzoylamino)butyl)-2-(R,S)-propylamino-1,2,3,4-tetrahydronaphthalene,
7-Fluoro-N-(4-(4-phenylbenzoylamino)butyl)-2-(R,S)-propylamino-1,2,3,4-tetrahydronaphthalene,
N-(4-(4-Phenylbenzoylamino)butyl)-2-(R,S)-propylamino-6-trifluoromethoxy-1,2,3,4-tetrahydronaphthalene,
5-Bromo-N-(4-(4-phenylbenzoylamino)butyl)-2-(R,S)-propylamino-1,2,3,4-tetrahydronaphthalene,
7-Bromo-N-(4-(4-phenylbenzoylamino)butyl)-2-(R,S)-propylamino-1,2,3,4-tetrahydronaphthalene,
6-Methanesulfonylmethyl-N-(4-(4-phenylbenzoylamino)butyl)-2-(R,S)-propylamino-1,2,3,4-tetrahydronaphthalene,
cis-5-Hydroxy-1-methyl-N-(4-(4-phenylbenzoylamino)butyl)-2-(R,S)-propylamino-1,2,3,4-tetrahydronaphthalene, 5-Methoxy-N-(4-(4-(2-pyrimidyl)benzoylamino)butyl-2-(R,S)-propylamino-1,2,3,4-tetrahydronaphthalene,
5-Methoxy-N-(4-(4-(3-pyridyl)benzoylamino)butyl )-2-(R,S)-propylamino-1,2,3,4-tetrahydronaphthalene,
5-Methoxy-N-(4-(4-(4-pyridyl)benzoylamino)butyl)-2-(R,S)-propylamino-1,2,3,4-tetrahydronaphthalene,
5-Methoxy-N-(4-(4-(5-pyrimidyl)benzoylamino)butyl)-2-(R,S)-propylamino-1,2,3,4-tetrahydronaphthalene,
5-Methoxy-N-(4-(4-(4-triazolyl)benzoylamino)butyl)-2-(R,S)-propylamino-1,2,3,4-tetrahydronaphthalene,
5-Methoxy-N-(4-(4-(1-triazolyl)benzoylamino)butyl)-2-(R,S)-propylamino-1,2,3,4-tetrahydronaphthalene,
5-Methoxy-N-(4-(4-pyridazylbenzoylamino)butyl)-2-(R,S)-propylamino-1,2,3,4-tetrahydronaphthalene,
N-(4-(4-Phenylbenzoylamino)butyl)-3-(R,S)-propylamino-8-trifluoromethanesulfonyloxy-3,4-dihydro-2H-benzopyran,
cis-1-Methyl-N-(4-(4-phenylbenzoylamino)butyl)-2-(R,S)-propylamino-5-trifluoromethanesulfonyloxy-1,2,3,4-tetrahydronapthalene,
5-Methanesulfonyloxy-N-(4-(4-phenylbenzoylamino)butyl)-2-(R,S)-propylamino-1,2,3,4-tetrahydronaphthalene,
N-(4-(4-Phenylbenzoylamino)butyl)-3-(R,S)-propylamino-8-methanesulfonyloxy-3,4-dihydro-2H-benzo[b]pyran,
7-Cyano-N-(4-(4-phenylbenzoylamino)butyl)-2-(R,S)-propylamino-1,2,3,4-tetrahydronaphthalene,
5-Cyano-N-(4-(4-phenylbenzoylamino)butyl)-2-(R,S)-propylamino-1,2,3,4-tetrahydronaphthalene,
6-Cyano-N-(4-(4-phenylbenzoylamino)butyl)-2-(R,S)-propylamino-1,2,3,4-tetrahydronaphthalene
7-(R,S)-(N-(4-(4-Phenylbenzoylamino)butyl)propylamino)-5,6,7,8-tetrahydronaphthalene-2-carboxamide
6-(R,S)-(N-(4-(4-Phenylbenzoylamino)butyl)propylamino)-5,6,7,8-tetrahydronaphthalene-1-carboxamide,
6-(R,S)-(N-(4-(4-Phenylbenzoylamino)butyl)propylamino)-5,6,7,8-tetrahydronapthalene-2-carboxamide
N,N-Dimethyl-(7-(R,S)-(N-(4-(4-phenylbenzoylamino)butyl)propylamino)-5,6,7,8-tetrahydronaphthalene)-2-carboxamide,
N,N-Dimethyl-(6-(R,S)-(N-(4-(4-phenylbenzoylamino)butyl)propylamino)-5,6,7,8-tetrahydronaphthalene)-2-carboxamide,
N-Methyl-(7-(R,S)-(N-(4-(4-phenylbenzoylamino)butyl)propylamino-5,6,7,8-tetrahydronaphthalene)-2-carboxamide,
6-Methylsulfonyl-N-(4-(4-phenylbenzoylamino)butyl)-2-(R,S)-propylamino-1,2,3,4-tetrahydronaphthalene;
N-(4-(4-Phenylbenzoylamino)butyl)-6-(R,S)-propylamino-5,6,7,8-tetrahydronaphthalene-1-acetic acid, ethyl ester;
N-(4-(4-Phenylbenzoylamino)butyl)-6-(R,S)-propylamino-5,6,7,8-tetrahydronaphthalene-2-acetic acid, ethyl ester;
N-(4-(4-Phenylbenzoylamino)butyl)-7-(R,S)-propylamino-5,6,7,8-tetrahydronaphthalene-2-acetic acid, ethyl ester;
and salts thereof.

The present invention also provides a process for preparing compounds of formula (I) which process comprises:

(a) reacting a compound of formula (II):

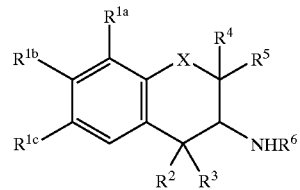

Formula (II)

wherein $R^{1a}$ to $R^6$ and X are as hereinbefore defined;
with a compound of formula (III):

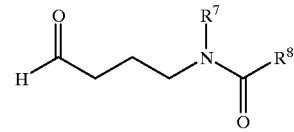

Formula (III)

wherein $R^7$ and $R^8$ are as hereinbefore defined;
(b) reacting a compound or formula (IV):

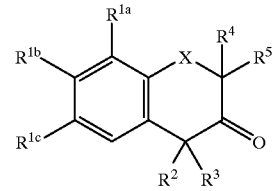

Formula (IV)

wherein $R^{1a}$ to $R^5$ and X are as hereinbefore defined;
with a compound of formula (V):

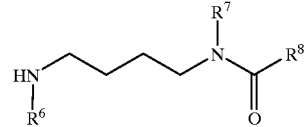

Formula (V)

wherein $R^6$, $R^7$ and $R^8$ are as hereinbefore defined;
(c) reaction of a compound of formula (VI):

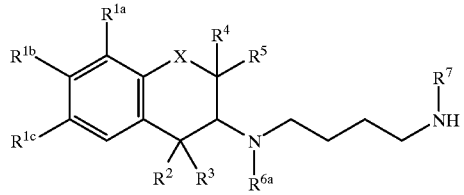

Formula (VI)

wherein $R^{6a}$ represents a $C_{1-6}$alkyl or aryl$C_{1-4}$alkyl group or an N-protecting group and $R^{1a}$ to $R^5$, $R^7$ and X are as hereinbefore defined;
with a compound of formula (VII):

R⁸COZ     Formula (VII)

wherein $R^8$ is as hereinbefore defined and Z is a halogen atom or the residue of an activated ester;

(d) reaction of a compound of formula (VIII):

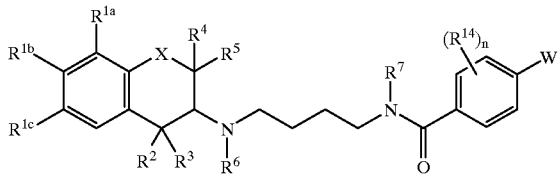

Formula (VIII)

wherein $R^{1a}$ to $R^7$, $R^{14}$ and n are as hereinbefore defined and W is a halogen atom or is a group M selected from a boronic acid function $B(OH)_2$ or a metal function such as trialkylstannyl e.g. $SnBu_3$, zinc halide or magnesium halide, with a compound $ArW^1$ wherein Ar is an optionally substituted phenyl group or an optionally substituted heterocyclic aromatic group as hereinbefore defined and $W^1$ is halogen when W is a group M or $W^1$ is a group M when W is halogen;

(e) interconversion of one compound of formula (I) to a different compound of formula (I) e.g. alkylation of a compound (I) wherein $R^6$ and/or $R^7$ represent hydrogen, or conversion of one or more of $R^{1a}$, $R^{1b}$ and $R^{1c}$ from alkoxy (e.g. methoxy) to hydroxy;

and optionally thereafter forming a salt of formula (I).

Processes (a) and (b) both require the presence of a reducing agent and may be carried out under similar conditions. Suitable reducing agents which may be employed include sodium borohydride, cyanoborohydride or triacetoxyborohydride under acidic conditions, or catalytic hydrogenation. The reaction may conveniently be effected in a solvent such as ethanol.

Process (c) may be effected by methods well known in the art for formation of an amide bond. It will be appreciated that to prepare a compound of formula (I) wherein $R^6$ represents hydrogen the corresponding nitrogen atom in formula (VI) should be protected by a group, represented above by $R^{6a}$, which can readily be removed at the end of the synthesis, e.g. an optionally substituted benzyl or benzyloxycarbonyl group, which groups may be removed by hydrogenation, or a t-butoxycarbonyl group which may be removed by treatment with acid e.g trifluoroacetic acid.

Reaction of a compound of formula (VIII) with $ArW^1$, according to process (d) may be effected in the presence of a transition metal eg palladium catalyst such as bis-triphenylphosphinepalladium dichloride or retrakis-triphenylphosphinepalladium (0). When M represents a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane. When M is a zinc or magnesium halide the reaction may be effected in an aprotic solvent such as tetrahydrofuran.

Interconversion reactions according to process (e) may be effected using methods well known in the art.

Compounds of formula (II) may be prepared by reacting a compound of formula (IV) as defined above, within an amine $R^6NH_2$, using conditions analogous to those described for processes (a) and (b). Compounds of formula (II) wherein one of $R^2$ and $R^3$ is an alkyl group may be prepared by the method described in Hacksell et al., J. Med. Chem. 1984 27 1003.

A compound of formula (VI) may be prepared by alkylation of an amine (II) by standard methods. Thus, for example a compound of formula (II) may be reacted with N-(4-bromobutylphthalimide) followed by removal of the phthalimide group to give a compound of formula (VI) where $R^7$ is hydrogen. Compounds where $R^7$ is alkyl may be prepared by subsequent reaction with the appropriate aldehyde using conditions analogous to processes (a) and (b) above.

Compounds of formula (IV) wherein X is $CH_2$, O, or a bond and $R^2$ to $R^5$ each represent hydrogen are well known or may be prepared by methods described in the literature. Thus for example when X is $CH_2$ and $R^{1a}$ or $R^{1b}$ represents methoxy a compound of formula (VI) may be prepared from 2,5-dimethoxynaphthalene or 2,7-dimethoxynaphthalene respectively, by reduction with sodium in ethanol followed by acid hydrolysis (J. W. Cornforth, R. Robinson, *J. Chem. Soc.*, (1949) 1855)

Compounds of formulae (III) and (V) are also known or may be prepared using standard procedures.

Compounds of formula (VIII) may be prepared by processes analogous to (a)–(c) described above. Compounds W-Ar are commercially available or may be prepared by standard methods.

When a compound of formula (I) is obtained as a mixture of enantiomers these may be separated by conventional methods such as crystallisation in the presence of a resolving agent, or chromatography, for example using a chiral HPLC column.

Compounds of formula (I) have been found to exhibit affinity for dopamine receptors, in particular the $D_3$ receptor, and are expected to be useful in the treatment of disease states which require modulation of such receptors, such as psychotic conditions. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347:146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors.

We have found that certain compounds of formula (I) are dopamine $D_3$ receptor antagonists, others are agonists and partial agonists. The functional activity of compounds of the invention (i.e. whether they are antagonists, agonists or partial agonists) can be readily determined using the test method described hereinafter, which does not require undue experimentation. $D_3$ antagonists are of potential use as antipsychotic agents for example in the treatment of schizophrenia, schizo-affective disorders, psychotic depression and mania. Conditions which may be treated by dopamine $D_3$ receptor agonists include dyskinetic disorders such as Parkinson's disease, neuroleptic-induced parkinsonism and tardive dyskinesias; depression; anxiety, memory disorders, sexual dysfunction and drug (eg. cocaine) dependency.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

A preferred use for $D_3$ antagonists according to the present invention is in the treatment of psychoses such as schizophrenia.

A preferred use for $D_3$ agonists according to the present invention is in the treatment of dyskinetic disorders such as Parkinson's disease.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pumpatomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants ($K_i$) of test compounds for displacement of [$^{125}$I] iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @ 37° C.), 20 mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @ 37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @ 37° C.). The final pellet was resuspended in 50 mM Tris salts (pH 7.4 @ 37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM [$^{125}$I] iodosulpride (~2000 Ci/mmol; Amersham, U. K.), and the test compound in a buffer containing 50 mM Tris salts (pH 7.4 @ 37° C.), 120 mM NaCl, 5 mM KCl, 2 mM $CaCl_2$, 1 mM $MgCl_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @ 37° C.), 120 mM NaCl, 5 mM KCl, 2 mM $CaCl_2$, 1 mM $MgCl_2$. The radioactivity on the filters was measured using a Cobra gamma counter (Canberra Packard). Non-specific binding was defined as the radioligand binding remaining after incubation in the presence of 100 $\mu$M iodosulpride. For competition curves, 14 concentrations (half-log dilutions) of competing cold drug were used. Competition curves were analysed simultaneously whenever possible using non-linear least-squares fitting procedures, capable of fitting one, two or three site models.

Compounds of Examples tested according to this method had pKi values in the range 6.7 to 9.7 at the human $D_3$ receptor.

Functional Activity at Cloned Dopamine Receptors

The functional activity of compounds at human D2 and human D3 receptors (ie agonism or antagonism) may be determined using a Cytosensor Microphysiometer (McConnell HM et al Science 1992 257 1906–1912) In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90s. The pump was on for the first 60s and the acidification rate determined between 68 and 88s, using the Cytosoft programme. Agonists and antagonists were diluted in running medium. In experiments to determine agonist activity, cells were exposed (4.5 min for hD2, 7.5 min for hD3) to increasing concentrations of putative agonist at half hour intervals. Seven concentrations of agonist were used. Peak acidification rate to each agonist concentration was determined and concentration-response curves fitted using Robofit [Tilford, N. S., Bowen, W. P. & Baxter, G. S. Br. J. Pharmacol. (1995) in press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Compounds of Examples 3j, 18, 18a, 19, 19a and 19b tested as agonists according to this method had pEC50 values in the range 8.0–11.0 at the human D3 receptor.

Compounds of Examples 2k, 2m, 2p, 2x, 3bb, 3cc, 3dd, 10f, 15, 17 tested as antagonists according to this method had pKb values in the range 8.0–10.5 at the human D3 receptor.

Pharmaceutical Formulations

The following represent typical pharmaceutical formulations according to the present invention, which may be prepared using standard methods.

IV Infusion

Compound of formula (I) 1–40 mg

Buffer to pH ca 7

Solvent/complexing agent to 100 ml

Bolus Injection

Compound of formula (I) 1–40 mg

Buffer to pH ca 7

Co-Solvent to 5 ml

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

Tablet

Compound 1–40 mg

Diluent/Filler* 50–250 mg

Binder 5–25 mg

Disentegrant* 5–50 mg

Lubricant 1–5 mg

Cyclodextrin 1–100 mg

* may also include cyclodextrins

Diluent: e.g. Microcrystalline cellulose, lactose, starch

Binder: e.g. Polyvinylpyrrolidone, hydroxypropymethylcellulose

Disintegrant: e.g. Sodium starch glycollate, crospovidone

Lubricant: e.g. Magnesium stearate, sodium stearyl fumarate.

Oral Suspension

Compound 1–40 mg

Suspending Agent 0.1–10 mg

Diluent 20–60 mg

Preservative 0.01–1.0 mg

Buffer to pH ca 5–8

Co-solvent 0–40 mg

Flavour 0.01–1.0 mg

Colourant 0.001–0.1 mg

Suspending agent: e.g. Xanthan gum, microcrystalline cellulose

Diluent: e.g. sorbitol solution, typically water

Preservative: e.g. sodium benzoate

Buffer: e.g. citrate

Co-solvent e.g. alcohol, propylene glycol, polyethylene glycol, cyclodextrin

The invention is further illustrated by the following non-limiting examples:

Description 1

N-(4-Hydroxybutyl)-4-phenylbenzamide

To a stirred solution of 4-amino-1-butanol (7.34 g, 82 mmol) and triethylamine (12.3 ml; 8.82 g, 87 mmol) in dichloromethane (100 ml) at 0° C. was added a solution of 4-phenylbenzoyl chloride (18.36 g, 85 mmol) in dichloromethane (800 ml) dropwise over 1.2 h. Resultant was stirred at 0° C. for 2 h then at room temperature for 18 h. The resulting white solid was filtered off (15.94 g) and the filtrate washed with 5% aqueous sodium hydroxide (1 L). The organic phase was dried (Na₂SO₄) and evaporated in vacuo to give a white solid (4.96 g) which was combined with the above to give the title compound (20.9 g, 93%).

¹H NMR (DMSO-d₆)δ: 1.4–1.7 (4H, m), 3.26 (2H, q, J=7 Hz), 3.42 (2H, q, J=7 Hz), 4.43 (1H, t, J=6 Hz), 7.35–7.55 (3H, m), 7.75 (4H, m), 7.94 (2H, d, J=9 Hz),8.52(1H, t, J=7 Hz)

Description 2

4-(4-Phenylbenzoylamino)butyraldehyde

To a mechanically-stirred solution of N-(4-hydroxybutyl)-4-phenylbenzamide (1 1.2 g, 44.2 mmol) and triethylamine (148 ml; 107.5 g, 1.06 mol) in dimethyl sulfoxide (250 ml) at room temperature was added, dropwise over 1 h, a solution of pyridine-sulfur trioxide complex (43.7 g, 0.273 mol) in dimethyl sulfoxide (200 ml) with external cooling using a cold water bath. The mixture was stirred at room temperature for 3 h, then 2M hydrochloric acid (550 ml) was added slowly with ice cooling. Resultant was diluted with water (1 L) then extracted with ethyl acetate (3×500 ml). The combined extracts were washed with 2M hydrochloric acid (3×500 ml) and water (3×500 ml) then dried (Na₂SO₄) and evaporated in vacuo to give a semi solid (12 g). Chromatography on silica gel eluting with 10–100% ethyl acetate-hexane gave the title compound as a white solid (4.72 g, 42%).

¹H NMR (CDCl₃) δ: 2.00 (2H, m), 2.65 (2H, m), 3.52 (2H, q, J=8 Hz), 6.54 (1H, br, m), 7.35–7.53 (3H, m), 7.54–7.71 (4H, m), 7.85 (2H, m), 9.83 (1H, s)

Description 3

(R,S)-2-Methylamino-1,2,3,4-tetrahydronaphthalene

To a stirred solution of 2-tetralone (1.0 g, 6.8 mmol) in ethanol (25 ml) was added a solution of methylamine in ethanol (8.03M; 2.4 ml; 19.2 mmol) followed by sodium cyanoborohydride (0.43 g, 6.8 mmol) and acetic acid (1.2 ml; 20.9 mmol). The reaction mixture was stirred at room temperature for 48 h, then poured into 5% aqueous sodium bicarbonate (150 ml) and extracted with dichloromethane (4×50 ml). The combined extracts were dried (Na₂SO₄) and evaporated in vacuo to give the title compound as an oil (0.88 g, 80%).

¹H NMR (CDCl₃) δ: 1.61 (1H, m), 1.71 (1H, br s), 2.07 (1H, m), 2.52 (3H, s), 2.59 (1H, dd, J=20, 12 Hz), 2.74–2.97 (3H, m), 3.03 (1H, dd, J=20, 5 Hz), 7.08 (4H, m)

Description 4

5-Methoxy-2-(R,S)-methylamino-1,2,3,4-tetrahydronaphthalene

Prepared from 5-methoxy-2-tetralone [J. W. Cornforth, R. Robinson, J. Chem. Soc. (1949) 1855] by the method of Description 3 in 60% yield.

¹H NMR (CDCl₃) δ: 1.64 (1H, m), 2.13 (1H, m), 2.54 (3H, s), 2.55–2.79 (3H, m), 2.83–2.96 (2H, m), 3.04 (1H, dd, J=20, 5 Hz), 3.80 (3H, s), 6.69 (2H, t, J=9 Hz), 7.10 (1H, t, J=9 Hz).

The following compounds were prepared in a similar manner to Description 4:
(a) 7-Methoxy-2-(R,S)-methylamino-1,2,3,4-tetrahydronaphthalene ¹H NMR (CDCl₃) δ: 1.40 (1H, br s), 1.57 (1H, m), 2.05 (1H, m), 2.50 (3H, s), 2.58 (1 H, dd, J=18, 9 Hz), 2.70–2.90 (3H, m), 2.98 (1H, dd, J=18, 4 Hz), 3.76 (3H, s), 6.62(1H, d, J=2 Hz), 6.69 (1H, dd, J=9,2 Hz), 7.00(1H, d J=9 Hz).

(b) 5-Methoxy-2-(R,S)-propylamino-1,2,3,4-tetrahydronaphthalene

¹H NMR (CDCl₃) δ: 0.94 (3H, t, J=7 Hz), 1.27 (1H, br, s), 1.54 (3H, m), 2.06 (1H, m), 2.47–2.73 (4H, m), 2.80–3.07 (3H, m), 3.80 (3H, s), 6.65 (1H, d, J=9 Hz), 6.71 (1H, d, J=9 Hz), 7.09 (1H, t, J=9 Hz).

(c) 8-Methoxy-3-(R,S)-methylamino-3,4-dihydro-2H-benzo [b]pyran

¹H NMR (CDCl₃) δ: 1.36 (1H, br s), 2.54 (3H, s), 2.66 (1H, dd, J=17, 8 Hz), 3.05 (2H, m), 3.86 (3H, s), 4.04 (1H, dd, J=11, 6 Hz), 4.27 (1H, m), 6.61–6.88 (3H, m).

(d) 6-Methoxy-2-(R,S)-methylamino-1,2,3,4-tetrahydronaphthalene ¹H NMR (CDCl₃) δ: 1.59 (1H, m), 1.75 (1H, br s), 2.05 (1H, m), 2.50 (3H, s), 2.60 (1H, m), 2.75–3.05 (4H, m,), 3.77 (3H, s), 6.66 (2H, m), 6.99 (1H, d, J=9 Hz).

(e) 6-Methoxy-3-(R,S)-methylamino-3,4-dihydro-2H-benzo [b]pyran

¹H NMR (CDCl₃) δ: 1.49 (1H, br s), 2.52 (3H, s), 2.65 (1H, dd, J=17, 8 Hz), 2.93–3.09 (2H, m), 3.84 (3H, s), 3.91 (1H, dd, J=11, 6 Hz), 4.14 (1H, m), 6.59 (1H, d, J=3 Hz), 6.66 (1H, dd, J=9, 3 Hz), 6.75 (1H, d, J=9 Hz).

(f) 8-Methoxy-3-(R,S)-propylamino-3,4-dihydro-2H-benzo [b]pyran

¹H NMR (CDCl₃) δ: 0.93 (3H, t, J=7 Hz), 1.52 (2H, tq, J=7, 7 Hz), 1.95 (1H, br s), 2.71 (3H, m), 3.03 (1H, dd, J=16, 4 Hz), 3.15 (1H, m), 3.87 (3H, s), 3.94 (1H, dd, J=11, 7 Hz), 4.29 (1H, m), 6.62–6.88 (3H, m).

(g) 5-Methoxy-2-(R,S)-ethylamino-1,2,3,4-tetrahydronaphthalene

¹H NMR (CDCl₃) δ: 1.15 (3H, t, J=7 Hz), 1.56 (1H, m), 2.06 (1H, m), 2.47–2.67 (2H, m), 2.75 (2H, q, J=7 Hz), 2.81–3.06 (4H, m), 3.80 (3H, s), 6.66 (1H, d, J=9 Hz), 6.70 (1H, d, J=9 Hz), 7.09 (1H, t, J=9Hz).

(h) 7-Methoxy-2-(R,S)-propylamino-1,2,3,4-tetrahydronaphthalene

¹H NMR (CDCl₃) δ: 0.95 (3H, t, J=7 Hz), 1.29 (1H, br s), 1.55 (3H, m), 2.05 (1H, m), 2.50–3.05 (7H, m), 3.75 (3H, s), 6.64 (1H, d, J=3 Hz), 6.69 (1H, dd, J=9, 3 Hz), 7.00 (1H, d J=9 Hz).

(i) 3-(R,S)-Propylamino-3,4-dihydro-2H-benzo[b]-pyran

¹H NMR (CDCl₃) δ: 0.93 (3H, t, J=7 Hz), 1.52 (2H, m), 1.96 (1H, s), 2.55–2.79 (3H, m), 2.92–3.28 (2H, m), 3.90 (1H, dd, J=11, 7 Hz), 4.20 (1H, dd, J=11, 3 Hz), 6.84 (2H, m), 7.05 (2H, m).

(j) 3-(R,S)-Methylamino-3,4-dihydro-2H-benzo[b]pyran

¹H NMR (CDCl₃) δ: 2.10–2.37 (1H br m), 2.53 (3H, s), 2.70 (1H, m), 2.94–3.15 (2H, m), 3.95 (1H, dd, J=11, 7 Hz), 4.21 (1H, m), 6.85 (2H, m), 7.06 (2H, m).

(k) 2-(R,S)-Propylamino-1,2,3,4-tetrahydronaphthalene

¹H NMR (CDCl₃) δ: 0.94 (3H, t, J=7 Hz), 1.54–1.84 (3H, m), 2.24 (1H, m), 2.69–3.00 (5H, m), 3.16 (1H, m), 3.32 (1H, m), 3.76 (2H, br s), 7.11 (4H, s).

(l) 2-Propylaminoindane

¹H NMR (CDCl₃) δ: 0.95 (3H, t, J=7 Hz), 1.40–1.60 (2H, m), 2.65 (2H, t, J=7 Hz), 2.75 (2H, dd, J=14, 7 Hz), 3.18 (2H, dd, J=14, 7 Hz), 3.62 (1H, dt, J=7, 7 Hz), 7.00–7.30 (4H, m).

(m) 2-(2-Propenyl)aminioindane

¹H NMR (CDCl₃) δ: 2.76 (2H, dd, J=14, 7 Hz), 3.17 (2H, dd, J=14, 7 Hz), 3.34 (2H, dd, J=7, 2 Hz), 3.67 (1H, dt, J=7, 7 Hz), 5.11 (1H, dd, J=10, 2 Hz), 5.20 (1H, dd, J=20, 2 Hz), 5.95 (1H, m), 7.15 (4H, m).

(n) 6-Methylsulfonylmethyl-2-(R,S)-propylamino-1,2,3,4-tetrahydronaphthalene

¹H NMR (CDCl₃) δ: 0.96 (3H, t, J=7 Hz), 1.40–1.68 (5H, m), 2.00–2.14 (1H, m), 2.52–3.09 (6H, m), 2.77 (3H, s), 4.19 (2H, s), 7.07–7.18 (3H, m).

(o) 6-Propylamino-5,6,7,8-tetrahydronaphthalene-1-acetic acid, ethyl ester.
(p) 6-Propylamino-5,6,7,8-tetrahydronaphthalene-2-acetic acid, ethyl ester.
(q) 7-Propylamino-5,6,7,8-tetrahydronaphthalene-2-acetic acid, ethyl ester.

Description 5

(2-Methoxy-N-(2-(5-methoxy-1,2,3,4-tetrahydro) naphthyl)-N-methyl-2-phenyl)acetamide (Diastereoisomer A) and (2-methoxy-N-(2-(5-methoxy-1,2,3,4-tetrahydro)naphthyl)-N-methyl-2-phenyl)acetamide (Diastereoisomer B)

To a stirred solution of 5-methoxy-2-(R,S)-methylamino-1,2,3,4-tetrahydronaphthalene (1.72 g, 9 mmol) and triethylamine (1,4 ml; 1.01 g, 10 mmol) in dichloromethane (30 ml) at room temperature under argon was added a solution of (S)-(2-methoxy-2-phenyl)acetyl chloride (1.82 g, 10 mmol) in dichloromethane (10 ml). The solution was stirred for 18 h then partitioned between saturated aqueous NaHCO₃ (100 ml) and dichloromethane (4×20 ml). The combined organic extracts were dried (Na₂SO₄) and evaporated in vacuo to give an oil (3.1 g). Chromatography on silica with 30% ethyl acetate—hexane elution gave a mixture of the two title compounds (1.66 g, 54%). Chromatography of this residue on solica (160 g) with 5–20% ethyl acetate—toluene gradient elution gave the title compounds as two separate diastereoisomers: The faster eluting diastereoisomer (Diastereoisomer A) (0.60 g, 20%).

HPLC: diastereomeric purity 96.3%.

Mass spectrum: found M⁺339.1832. C₂₁H₂₅NO₃ requires 339.1835

The slower eluting diastereoisomer (Diastereoisomer B) (0.60 g, 20%) HPLC: diastereomeric purity 86.6% Mass spectrum: found M⁺339.1832. C₂₁H₂₅NO₃ requires 339.1835

Description 6

(R or S)-5-Methoxy-N-2-methylamino-1,2,3,4-tetrahydronaphthalene (Enantiomer A)

To a stirred solution of (2-methoxy-N-(2-(5-methoxy-1,2,3,4-tetrahydro)naphthyl-N-methyl-2-phenyl)acetamide (Diastereoisomer A) (0.58 g, 1.71 mmol) in dry tetrahydrofuran (30 ml) at room temperature under argon was added potassium t-butoxide (8.56 g, 76 mmol) and water (0.14 ml, 7.8 mmol). The reaction mixture was stirred at room temperature for 64 h, then filtered. The filtrate was partitioned between water (100 ml) and ether (3×50 ml). The organic extracts were dried, then treated with HCl-ether. The resulting solid was filtered off to give the hydrochloride salt of the title compound. The solid was partitioned between saturated aqueous NaHCO₃ (50 ml) and dichloromethane (3×50 ml). The combined organic extracts were dried (Na₂SO₄) and evaporated in vacuo to give the title compound (0.25 g, 77%) as an oil.

¹H NMR (CDCl₃) δ: 2.07 (1H, m), 2.45–2.75 (2H, m), 2.78 (3H, br s), 3.10 (1H, m), 3.15–3.45 (3H, m), 3.81 (3H, s), 6.68 (2H, m), 7.11 (1H, t, J=9 Hz), 9.80 (2H, br s). (.HCl salt)

Description 7

(R or S)-5-Methoxy-2-methylamino-1,2,3,4-tetrahydronaphthalene (Enantiomer B)

Prepared from (2-methoxy-N-(2-(5-methoxy-1,2,3,4-tetrahydro)naphthyl)-N-methyl-2-phenyl)acetamide (Diastereoisomer B) using the method of Description 6, in 82% yield.

¹H NMR (CDCl₃) δ: 2.04 (1H, m), 2.42–2.73 (2H, m), 2.78 (3H, br s), 3.10 (1H, m), 3.15–3.40 (3H, m), 3.81 (3H, s), 6.68 (2H, m), 7.11 (1H, t, J=9Hz), 9.80 (2H, br s). (.HCl salt).

Description 8

N-(4-Aminobutyl)-7-methoxy-2-(R,S)-methylamino-1,2,3,4-tetrahydronaphthalene

A mixture of 7-methoxy-2-(R,S)-methylamino-1,2,3,4-tetrahydronaphthalene (3.02 g, 15.9 mmol), N-(4-bromobutyl)phthalimide (4.82 g, 17.1 mmol), anhydrous potassium carbonate (4.80 g, 34.7 mmol) and dry dimethylformamide (75 ml) was heated at 60° C. for 2 h, then left at room temperature for 18 h. Excess solvent was evaporated in vacuo, and the residue was partitioned between water (200 ml) and dichloromethane (3×100 ml). The organic phase was dried (Na₂SO₄) then evaporated in vacuo to give an oil. Chromatography on silica with 0–5% methanol-dichloromethane elution gave the intermediate phthalimide (3.8 g) as an oil which solidified. The latter was dissolved in ethanol (20 ml) and treated with hydrazine hydrate (2 ml; excess). Stirring at room temperature was carried out for 18 h, followed by reflux for 1 h. The mixture was cooled to 0° C., then filtered. The filtrate was evaporated in vacuo and the residue dissolved in dichloromethane (50 ml). Anhydrous sodium sulfate was added, and the mixture was filtered through kieselguhr. The filtrate was evaporated in vacuo to give the title compound (1.90 g, 46%).

¹H NMR (CDCl₃) δ: 1.40–1.72 (7H, m), 2.04 (1H, m), 2.33 (3H, s), 2.54 (2H, t, J=5 Hz), 2.65–2.95 (7H, m), 3.77 (3H, s), 6.64 (1H, d, J=3 Hz), 6.68 (1H, dd, J=9, 3 Hz), 6.98 (1H, d, J=9 Hz).

The following compounds were prepared in a similar manner to Description 8:

(a) N-(4-Aminobutyl)-2-(R,S)-propylamino-1,2,3,4-tetrahydronaphthalene

Mass spectrum (API⁺): 261 (MH⁺, 100%), 190 (50%), 128 (15%). C₁₇H₂₈N₂ requires 260.

(b) N-(4-Aminobutyl)-5-methoxy-2-(R,S)-propylamino-1,2,3,4-tetrahydronaphthalene Mass spectrum (API⁺): 291 (MH⁺, 100%), 220 (100%). C₁₈H₃₀N₂O requires 260.

Description 9

7-Methoxy-N-(4-(4-bromobenzoyl)amino)butyl-2-(R,S)-methylamino-1,2,3,4-tetrahydronaphthalene A mixture of N-(4-aminobutyl)-7-methoxy-2-(R,S), methylamino-1,2,3,4-tetrahydronaphthalene (8.4 g, 32 mmol), diisopropylethylamine (5.6 ml; 32 mmol) and 4-bromobenzoyl chloride (7.02 g, 32 mmol) in dichloromethane (150 ml) was stirred at room temperature for 18 h, then partitioned between saturated aqueous NaHCO₃ (200 ml) and dichloromethane (3×5 ml). The combined organic extracts were dried (Na₂SO₄) then evaporated in vacuo to give an oil. Flash chromatography on silica with 2–10% methanol-dichloromethane gradient elution gave the title compound (12.34 g, 86%). Mass spectrum: found M⁺444.1405. C₂₃H₂₉N₂O₂⁷⁹Br requires 444.1412.

Description 10

7-Hydroxy-N-(4-(4-bromobenzoyl)amino)butyl-2-(R,S)-methylamino-1,2,3,4-tetrahydronaphthalene A mixture of 7-methoxy-N-(4-(4-bromobenzoyl)amino) butyl-2-(R,S)-methylamino-1,2,3,4-tetrahydronaphthalene (1.24 g, 2.8 mmol), dichloromethane (28 ml) and a solution of boron tribromide in dichloromethane (1M; 16.3 ml) was stirred at room temperature for 3 h, then poured onto a mixture of crushed ice (200 g) and 0.880 ammonia (50 ml). The resulting mixture was stirred vigorously for 0.5 h then extracted with dichloromethane (3×50 ml). The combined extracts were dried ($Na_2SO_4$) then evaporated in vacuo to give the title compound (1.20 g, 100%) as an oil.

Mass spectrum: found $M^+$430.1266. $C_{22}H_{27}N_2O_2{}^{79}Br$ requires 430.1255.

Description 11

N-(4-Aminobutyl)-7-hydroxy-2-(R,S)-methylamino-1,2,3,4-tetrahydronaphthalene, dihydrobromide A mixture of N-(4-aminobutyl)-7-methoxy-2-(R,S)-methylamino-1,2,3,4-tetrahydronaphthalene (0.79 g, 3.0 mmol) and aqueous HBr (48%; 20 ml) was heated at reflux for 5 h, then evaporated in vacuo to give the title compound (1.2 g, 100%).

Mass spectrum ($API^+$): 249 ($MH^+$, 100%), 232 (10%), 178 (20%) $C_{15}H_{24}N_2O$ requires 248.

Description 12

7-Methoxy-N-(4-(4-tributylstannyl)benzoylamino) butyl-2-(R,S)-methylamino-1,2,3,4-tetrahydronaphthalene A mixture of 7-methoxy-N-(4-(4-bromobenzoyl)amino) butyl-2-(R,S)-methylamino-1,2,3,4-tetrahydronaphthalene (5.0 g, 11 mmol), tetrakis-triphenylphosphinepalladium (0) (1.29 g, 1.11 mmol), xylene (45 ml) and hexabutyldistannane (9.78 g, 16.9 mmol) was heated at reflux under argon for 2 h, then cooled and partioned between water (150 ml) and ethyl acetate (3×50 ml). The combined extracts were dried ($Na_2SO_4$) then evaporated in vacuo to give an oil. Chromatography on silica with 2–8% methanol-dichloromethane gradient elution gave the title compound (3.04 g, 41%) as a yellow oil.

$^1$H NMR ($CDCl_3$) δ: 0.89 (9H, t, J=7 Hz), 1.07 (6H, m), 1.33 (6H, m), 1.52 (6H, m), 1.60–2.02 (5H, m), 2.27 (1H, m), 2.58 (3H, s), 2.66–3.18 (6H, m), 3.30 (1H, m), 3.49 (2H, m), 3.74 (3H, s), 6.61 (1H, d, J=3 Hz), 6.70 (1H, dd, J=9, 3 Hz), 6.97 (1H, d, J=9 Hz), 7.30 (1H, br m), 7.50 (2H, d, J=9 Hz), 7.79 (2H, d, J=9 Hz).

Description 13

(4-(3-(5-Methyl(1,2,4-oxadiazolyl)))-2-methyl) phenylbenzoyl chloride

Prepared according to the method described in EP 0 533 268 A1

Description 14

8-Methoxy-3,4-dihydro-2H-benzo[b]pyran-3-one

Prepared according to the method described in L. D. Wise et al., J. Med. Chem., 1988 31 688

The following compounds were prepared in a similar manner to Description 14:
(a) 6-Methoxy-3,4-dihydro-2H-benzo[b ]pyran-3-one (b) 3,4-Dihydro-2H-benzo[b]pyran-3-one

Description 15 cis-5-Methoxy-1-methyl-2-(R,S)-propylamino-1,2,3,4-tetrahydronaphthalene

Prepared by the method described in Hacksell et al., J. Med. Chem. 1984 27 1003.

Description 16

6-(Methanesulphonylmethyl)-2-tetralone

Stage 1

A mixture of 6-bromo-2-tetralone (8.80 g, 39 mmol), trimethyl orthoformate (17.2 ml, 157 mmol), ethylene glycol (16.2 ml, 290 mmol) and p-toluenesulfonic acid (0.07 g, 0.37 mmol) in dry dichloromethane (200 ml) was stirred at room temperature for 18 h, then partitioned between saturated aqueous $NaHCO_3$ (100 ml) and dichloromethane (2×50 ml). The combined organic extracts were dried ($Na_2SO_4$) then evaporated in vacuo to give an oil. Column chromatography on silica with 0–10% diethyl ether-hexane gradient elution gave 6-bromo-2-tetralone ethylene ketal as a yellow oil (8.84 g, 84%).

Stage 2

To a stirred solution of 6-bromo-2-tetralone ethylene ketal (8.8 g, 33 mmol) and TMEDA (4.9 ml, 33 mmol) in dry THF (100 ml) at −70° C. under argon was added "BuLi (1.6M, 21.8 ml, 35 mmol) dropwise. Resultant was stirred at −70° C. for 45 min. and then treated with dry DMF (5.3 ml, 68 mmol). Resultant was stirred at −70° C. for 1 h, then at 0° C. for 1.5 h and room temperature for 2 h. The mixture was partitioned between saturated aqueous $NH_4Cl$ (100 ml) and diethyl ether (2×100 ml). The combined organic extracts were washed with brine (100 ml), dried ($Na_2SO_4$) then evaporated in vacuo to a brown oil. Column chromatography on silica with 5–30% diethyl ether-hexane gradient elution gave the aldehyde as a yellow oil (4.79 g, 67%).

Stage 3

To a stirred solution of the aldehyde (from Stage 2) (4.71 g, 22 mmol) in ethanol (140 ml) under argon was added sodium borohydride (1.11 g, 29 mmol) in one portion. Resultant was stirred at room temperature for 2 h, and then treated with saturated aqueous $NH_4Cl$ over 15 min. Ethanol was evaporated in vacuo and the residue was partitioned between 0.5M aqueous NaOH (250 ml) and ethyl acetate (2×400 ml). Combined organic extracts were washed with brine (250 ml), dried ($Na_2SO_4$) then evaporated in vacuo to afford the alcohol as an orange oil (4.44 g, 93%).

Stage 4

To a stirred solution of the alcohol (from Stage 3) (3.34 g, 15 mmol) and triethylamine (2.3 ml, 17 mmol) in dry dichloromethane (30 ml) at 0° C. under argon, was added dropwise a solution of methansulfonyl chloride (1.3 ml, 17 mmol) in dry dichloromethane (60 ml). Resultant was stirred at 0° C. for 1 h and then poured into chilled 10% citric acid (100 ml) and extracted with dichloromethane (2×50 ml). Combined organic extracts were dried ($Na_2SO_4$) and evaporated in vacuo to afford the methanesulfonate as a pale brown oil (4.67 g, 100%).

Stage 5

To a stirred solution of the methanesulfonate (from Stage 4) (4.67 g, 16 mmol) in dry acetone (100 ml) at 0° C. under argon was added sodium iodide (3.88 g, 26 mmol) portionwise. Resultant was warmed to room temperature over 1 h, water (100 ml) was then added and the mixture was evaporated in vacuo to ½ volume. Resultant was extracted with dichloromethane (2×100 ml) and combined organic extracts were dried ($Na_2SO_4$) and evaporated to a brown oil (4.29 g) which was used without further purification in Stage 6.

Stage 6

To a stirred suspension of sodium thiomethoxide (0.95 g, 14 mmol) in dry methanol (35 ml) to 0° C. under argon was added a solution of the iodide (from Stage 5) (3.74 g, 11 mmol) in dry acetone (70 ml) dropwise. Resultant was stirred at 0° C. for 0.5 h and then poured into water (70 ml) and extracted with ethyl acetate (2×100 ml). Combined organic extracts were dried (Na$_2$SO$_4$) and evaporated in vacuo to a brown oil. Chromatography on silica with 5–10% ethyl acetate-hexane gradient elution afforded the methyl sulfide as a pale yellow oil (1.12 g, 41%).

Stage 7

To a stirred suspension of the methyl sulfide (from Stage 6) (1.12 g, 4.5 mmol) and sodium hydrogen carbonate (0.87 g, 10 mmol) in dry dichloromethane (60 ml) at 0° C. under argon was added portionwise MCPBA (57–86%, 2.52 g). Resultant was stirred at room temperature for 2 h. Dichloromethane (40 ml) was added and the organic layer washed successively with 1M aqueous NaOH (2×5 ml) and brine (50 ml) and then dried (Na$_2$SO$_4$) and evaporated in vacuo to afford the methyl sulfone as a white solid (1.29 g, 100%).

Stage 8

To a stirred solution of the product from Stage 7 (1.16 g, 4 mmol) in dry THF (30 ml) at room temperature under argon was added dropwise 2M HCl (18 ml, 36 mmol). The mixture was stirred at room temperature for 4 h, and then evaporated to ½ volume and treated with water (30 ml). Basification with solid K$_2$CO$_3$ followed by extraction with dichloromethane (2×50 ml), drying (Na$_2$SO$_4$) and evaporation of the organic extracts in vacuo afforded the title compound as a yellow oil (0.97 g, 99%).

$^1$H NMR (CDCl$_3$) δ: 2.59 (2H, t, J=8 Hz), 2.81 (3H, s), 3.12 (2H, t, J=8 Hz), 3.60 (2H, s), 4.25 (2H, s), 7.13–7.30 (2H, m), 7.33 (1H, br s)

Description 17

6-Bromo-2-tetralone

Prepared following a procedure similar to that used in EP 0564193. The following compounds were prepared in a manner similar to Description 17.
(a) 5-Bromo-2-tetralone
(b) 7-Bromo-2-tetralone
(c) 5-Chloro-2-tetralone
(d) 6-Chloro-2-tetralone
(e) 7-Chloro-2-tetralone
(f) 5-Trifluoromethoxy-2-tetralone
(g) 6-Trifluoromethoxy-2-tetralone
(h) 5-Fluoro-2-tetralone
(i) 6-Fluoro-2-tetralone
(j) 7-Fluoro-2-tetralone
(k) 6-Methylthio-2-tetralone
(l) 7-Methylthio-2-tetralone
(m) 6-Oxo-5,6,7,8-tetrahydronaphthalene-1-acetic acid, ethyl ester.
(n) 6-Oxo-5,6,7,8-tetrahydronaphthalene-2-acetic acid, ethyl ester.
(o) 7-Oxo-5,6,7,8-tetrahydronaphthalene-2-acetic acid, ethyl ester.

EXAMPLE 1

N-(4-(4-Phenylbenzoylamino)butyl)-2-(R,S)-methylamino-1,2,3,4-tetrahydronaphthalene, hydrochloride A mixture of 4-(4-Phenylbenzoylamino)butyraldehyde (0.30 g, 1.12 mmol), (R,S)-2-methylamino-1,2,3,4-tetrahydronaphthalene (0.23 g, 1.43 mmol) and sodium cyanoborohydride (0.072 g, 1.14 mmo) in ethanol (20 ml) was treated with acetic acid (10 drops) and stirred at room temperature for 24 h. Reaction mixture was poured into 5% aqueous sodium hydrogen carbonate (100 ml) then extracted with dichloromethane (3×30 ml). The combined extracts were dried (Na2SO4) then evaporated in vacuo to give an oil (0.48 g). Chromatography on silica gel eluting with ethyl acetate containing 0–5% methanol gave an oil (0.34 g) which was treated with ethereal HCl and dichloromethane to afford the title compound as a white solid (0.33 g, 65%)

Mass Spectrum: Found M+ 412.2530. C28H32N2O requires 412.2515

EXAMPLE 2

5-Methoxy-N-(4-(4-phenylbenzoylamino)butyl)-2-(R,S)-methyl-amino-1,2,3,4-tetrahydronaphthalene, hydrochloride Prepared from 5-methoxy-2-(R,S)-methylamino-1,2,3,4-tetrahydronaphthalene by the method of Example 1 in 52% yield.

Mass Spectrum: Found M+ 442.2620. C29H34N2O2 requires 442.2620

The following compounds were prepared in a similar manner to Example 2:
(a) 7-Methoxy-N-(4-(4-phenylbenzoylamino)butyl)-2-(R,S)-methylamino-1,2,3,4-tetrahydronaphthalene, hydrochloride Found C, 71.93; H, 7.19; N, 5.87. C29H34N2O2.HCl.0.25H2O requires C, 71.95; H, 7.40; N, 5.79%.

Mass spectrum: found M+ 442.2617. C29H34N2O2 requires 442.2620.
(b) 5-Methoxy-N-(4-(4-phenylbenzoylamino)butyl)-2-(R,S)-propylamino-1,2,3,4-tetrahydronaphthalene, hydrochloride Mass spectrum: found M$^+$ 470.2925. C$_{31}$H$_{38}$N$_2$O$_2$ requires 470.2933.
(c) 8-Methoxy-N-(4-(4-phenylbenzoylamino)butyl)-3-(R,S)-methylamino-3,4-dihydro-2H-benzo[b]pyran, hydrochloride mp 103–105° C.

$^1$H NMR (CDCl$_3$) δ: 1.54–1.76 (4H, m), 2.33 (3H, s), 2.62 (2H, t, J=6 Hz), 2.85 (2H, d, J=6 Hz), 3.05 (1H, m), 3.48 (2H, q, J=6 Hz), 3.85 (3H, s), 3.94 (1H, t, J=12 Hz), 4.44 (1H, dd, J=12, 3 Hz), 6.55–6.76 (3H, m), 6.82 (1H, t, J=9 Hz), 7.43 (3H, m), 7.62 (4H, m), 7.82 (2H, d, J=9 Hz). (Free base)
(d) 6-Methoxy-N-(4-(4-phenzylbenzoylamino)butyl)-2-(R,S)-methylamino-1,2,3,4-tetrahydronaphthalene, hydrochloride Mass spectrum: found M$^+$ 442.2613 C$_{29}$H$_{34}$N$_2$O$_2$ requires 442.2620.
(e) 6-Methoxy-N-(4-(4-phenylbenzoylamino)butyl)-3-(R,S)-methylamino-3,4-dihydro-2H-benzo[b]pyran mp 88–90° C.

$^1$H NMR (CDCl$_3$) δ: 1.62 (4H, m), 2.32 (3H, s), 2.59 (2H, m), 2.83 (2H, m), 3.00 (1H, m), 3.48 (2H, m), 3.70 (3H, s), 3.84 (1H, t, J=12 Hz), 4.26 (1H, d, J=12 Hz), 6.55–6.79 (4H, m), 7.41 (3H, m), 7.60 (4H, m), 7.83 (2H, d, J=9 Hz).
(f) 8-Methoxy-N-(4-(4-phenylbenzoylamino)butyl)-3-(R,S)-propylamino-3,4-dihydro-2H-benzo[b]pyran, hydrochloride Mass spectrum (API$^+$): 473 (MH$^+$, 100%), 277 (5%) C$_{30}$H$_{36}$N$_2$O$_3$ requires 472.
(g) 5-Methoxy-N-(4-(4-phenylbenzoylamino)butyl)-2-(R,S)-ethylamino-1,2,3,4-tetrahydronaphthalene, hydrochloride Mass spectrum: found M$^+$ 456.2768. C$_{30}$H$_{36}$N$_2$O$_2$ requires 456.2777.
(h) 7-Methoxy-N-(4-(4-phenylbenzoylamino)butyl-2-(R,S)-propylamino-1,2,3,4-tetrahydronaphthalene, hydrochloride Mass spectrum: found M⁺ 470.2948. $C_{31}H_{38}N_2O_2$ requires 470.2933.

(i) N-(4-(4-Phenylbenzoylamino)butyl)-3-(R,S)-propylamino-3,4-dihydro-2H-benzo[b]pyran, hydrochloride Mass spectrum: found M⁺ 442.2630. $C_{29}H_{34}N_2O_2$ requires 442.2620.

(j) N-(4-(4-Phenylbenzoylamino)butyl)-3-(R,S)-methylamino-3,4-dihydro-2H-benzo[b]pyran, hydrochloride Mass spectrum: found M+ 414.2285. C27H30N2O2 requires 414.2307.

(k) 5-Chloro-N-(4-(4-phenylbenzoylamino)butyl)-2-(R,S)-propylamino-1,2,3,4-tetrahydronaphthalene, hydrochloride
mp 103–5° C.

1H NMR (DMSO-d6): 0.93 (3H, t, J=7 Hz), 1.64 (2H, m), 1.78 (5H, m), 2.36 (1H, m), 2.74 (1H, m), 2.90–3.40 (9H, m), 3.67 (1H, m), 7.13 (1H, d, J=9 Hz), 7.19 (1H, t, J=9 Hz), 7.29 (1H, d, J=9 Hz), 7.41 (1H, m), 7.50 (2H, t, J=9 Hz), 7.73 (4H, m), 7.96 (2H, m), 8.63 (1H, br m) 10.11 (1H, br s).

IR v=o 1642

Mass spectrum: found M+ 474.2426. C30H35ClNO2 requires 474.2437.

(l) 6-Fluoro-N-(4-(4-phenylbenzoylamino)butyl)-2-(R,S)-propylamino-1,2,3,4-tetrahydronaphthalene, hydrochloride Mass spectrum: found M+ 458.2723. C30H35FN2O requires 458.2733.

(m) 7-Chloro-N-(4-(4-phenylbenzoylamino)butyl)-2-(R,S)-propylamino-1,2,3,4-tetrahydronaphthalene, hydrochloride Mass spectrum: found M+ 474.2426. C30H35ClN2O requires 474.2437

(n) 6-Chloro-N-(4-(4-phenylbenzoylamino)butyl)-2-(R,S)-propylamino-1,2,3,4-tetrahydronaphthalene, hydrochloride Mass spectrum: found M⁺ 474.2445. $C_{30}H_{35}ClN_2O$ requires 474.2437.

(o) 6-Bromo-N-(4-(4-phenylbenzoylamino)butyl)-2-(R,S)-propylamino-1,2,3,4-tetrahydronaphthalene ¹H NMR (CDCl₃) δ: 0.89 (3H, t, J=7 Hz), 1.46 (2H, m), 1.52–1.73 (6H, m), 2.45 (2H, m), 2.56 (1H, m), 2.63–2.86 (4H, m), 2.94 (1H, m), 3.51 (2H, q, J=6 Hz), 6.47 (1H, br m), 6.93 (1H, d, J=9 Hz), 7.19 (2H, m), 7.45 (3H, m), 7.63 (4H, m), 7.84 (2H, d, J=9 Hz).

(p) N-(4-(4-Phenylbenzoylamino)butyl)-2-propylaminoindane, hydrochloride

¹H NMR (DMSO d₆) δ: 0.92 (3H, t, J=7 Hz), 1.55–1.9 (6H, m), 3.0–3.1 (2H, m), 3.1–3.2 (2H, m), 3.2–3.5 (6H, m), 4.1–4.3 (1H, m), 7.1–7.3 (4H, m), 7.3–7.6 (3H, m), 7.73 (2H, d, J=7 Hz), 7.77 (2H, d, J=7 Hz), 7.97 (2H, d, J=8 Hz), 8.5–8.7 (1H, m), 10.89 (1H, br s).

(q) N-(4-(4-Phenylbenzoylamino)butyl-2-(2-propenyl) aminoindane

¹H NMR (CDCl₃) δ: 1.65 (4H, m), 2.59 (2H, t, J=7 Hz), 2.88 (2H, dd, J=16, 9 Hz), 3.04 (2H, dd, J=16, 9 Hz), 3.23 (2H, d, J=7 Hz), 3.50 (2H, q, J=7 Hz), 3.69 (1H, dt, J=9, 9 Hz), 5.65 (1H, d, J=10 Hz), 5.68 (1H, dd, J=20, 2 Hz), 5.91 (1H, m), 6.66 (1H, br, m), 7.14 (4H, m), 7.45 (3H, m), 7.57 (4H, m), 7.84 (2H, d, J=9 Hz).

(r) cis-5-Methoxy-1-methyl-N-(4-(4-phenylbenzoylamino)butyl)-2-(R,S)-propylamino-1,2,3,4-tetrahydronaphthalene hydrochloride Mass spectrum: found M⁺ 484.3061. $C_{32}H_{40}N_2O_2$ requires 484.3090.

(s) N-(4-(4-Phenylbenzoylamino)butyl)-2-(R,S)-propylamino-5-trifluoromethoxy-1,2,3,4-tetrahydronaphthalene, hydrochloride ¹H NMR (DMSO-d₆) δ: 0.92 (3H, t, J=7 Hz), 1.64 (2H, m), 2.81 (5H, m), 2.37 (1H, m), 2.73 (1H, m), 3.03 (2H, m), 3.18 (3H, m), 3.31 (4H, m), 3.70 (1H, m), 7.19 (2H, d), 7.30 (1H, m), 7.40 (1H, m), 7.49 (2H, t, J=9 Hz), 7.74 (4H, m), 7.95 (2H, d, J=9 Hz), 8.62 (1H, m), 10.14 (1H, s).

(t) 6-Methylthio-N-(4-(4-phenylbenzoylamino)butyl)-2-(R,S)-propylamino-1,2,3,4-tetrahydronaphthalene, hydrochloride ¹H NMR (DMSO-d₆) δ: 0.95 (3H, t, J=7 Hz), 1.52–1.95 (8H, m), 2.31 (1H, m), 2.43 (3H, m), 2.79–3.45 (1H, m), 3.55–3.75 (1H, m), 7.05 (2H, d, J=9 Hz), 7.37–7.55 (3H, m), 7.75 (4H, t, J=9 Hz), 7.95 (2H, d, J=9 Hz), 8.65 (1H, m), 10.15 (1H, br s).

(u) 5-Fluoro-N-(4-(4-phenylbenzoylamino)butyl)-2-(R,S)-propylamino-1,2,3,4-tetrahydronaphthalene, hydrochloride ¹H NMR (CDCl₃) δ: 1.00 (3H, s), 1.90 (2H, m), 2.01 (4H, m), 2.15 (1H, m), 2.56 (1H, m), 2.70 (1H, m), 3.09 (5H, m), 3.33 (2H, m), 3.61 (2H, m), 6.84 (2H, m), 7.08 (1H, m), 7.36 (1H, m), 7.44 (2H, t, J=9 Hz), 7.59 (2H, d, J=9 Hz), 7.71 (3H, m), 7.85 (1H, br s), 8.08 (2H, s), 9.83 and 11.78 (1H, br s)

(v) 7-Methylthio-N-(4-(4-phenylbenzoylamino)butyl)-2-(R,S)-propylamino-1,2,3,4-tetrahydronaphthalene, hydrochloride ¹H NMR (DMSO-d₆) δ: 0.92 (3H, t, J=7 Hz), 1.63 (2H, m), 1.79 (5H, m), 2.30 (1H, m), 2.43 (3H, s), 2.83 (2H, m), 3.07 (2H, m), 3.17 (2H, m), 3.24 (2H, m), 3.34 (2H, m), 3.64 (1H, m), 7.04 (3H, m), 7.41 (1H, m), 7.49 (2H, m), 7.72 (4H, m), 7.96 (2H, d, J=9 Hz), 8.62 (1H, m), 10.13 (1H, s).

(w) 7-Fluoro-N-(4-(4-phenylbenzoylamino)butyl)-2-(R,S)-propylamino-1,2,3,4-tetrahydronaphthalene, hydrochloride ¹H NMR (CDCl₃) δ: 1.00 (3H, m), 1.66 (4H, m), 2.02 (6H, m), 2.55 (1H, m), 3.06 (7H, m), 3.62 (2H, m), 6.77 (1H, m), 6.84 (1H, t, J=9 Hz), 7.01 (1H, m), 7.37 (1H, m), 7.44 (2H, t), 7.60 (2H, d, J=9 Hz), 7.70 (2H, m), 8.08 (2H, s), 9.85 and 11.82 (1H, br s).

(x) N-(4-(4-Phenylbenzoylamino)butyl)-2-(R,S)-propylamino-6-trifluoromethoxy-1,2,3,4-tetrahydronaphthalene, hydrochloride ¹H NMR (DMSO-d₆) δ: 0.95 (3H, t, J=7 Hz), 1.63–1.99 (8H, m), 2.36 (1H, m), 2.78–3.40 (9H, m), 3.68 (1H, m), 7.09 (2H, s), 7.23 (1H, m), 7.43 (3H, m), 7.70 (4H, m), 7.94 (2H, d, J=9 Hz), 8.42 (1H, m), 10.45 (1H, br s).

(y) 5-Bromo-N-(4-(4-phenylbenzoylamino)butyl)-2-(R,S)-propylamino-1,2,3,4-tetrahydronaphthalene, hydrochloride Mass spectrum: found M⁺ 518.1928. $C_{30}H_{35}BrN_2O$ requires 518.1932.

(z) 7-Bromo-N-(4-(4-phenylbenzoylamino)butyl)-2-(R,S)-propylamino-1,2,3,4-tetrahydronaphthalene, hydrochloride.

Mass spectrum: found M⁺ 518.1922. $C_{30}H_{35}BrN_2O$ requires 518.1932.

(aa) 6-Methanesulfonylmethyl-N-(4-(4-phenylbenzoylamino)butyl)-2-(R,S)-propylamino-1,2,3,4-tetrahydronaphthalene, hydrochloride ¹NMR (CDCl₃) δ: 0.96 (3H, t, J=7 Hz), 1.58–1.92 (6H, m), 2.20–2.35 (1H, m), 2.40–2.54 (1H, m), 2.77–3.48 (11H, m), 2.90 (3H, s), 4.42 (2H, s), 7.15 (4H, m), 7.38–7.55 (2H, m), 7.70–7.80 (4H, m), 7.95 (2H, d, J=9 Hz), 8.65 (1H, m), 8.98 (1H, br s).

(bb) N-(4-(4-Phenylbenzoylamino)butyl)-6-(R,S)-propylamino-5,6,7,8-tetrahydronaphthalene-1-acetic acid, ethyl ester, hydrochloride.

Mass Spectrum (API+): Found MH+ 527. C34H42N2O3 requires 526.

(cc) N-(4-(4-Phenylbenzoylamino)butyl)-6-(R,S)-propylamino-5,6,7,8-tetrahydronaphthalene-2-acetic acid, ethyl ester, hydrochloride.

Mass Spectrum (API+): Found MH+ 527. C34H42N2O3 requires 526.

(dd) N-(4-(4-Phenylbenzoylamino)butyl)-7-(R,S)-propylamino-5,6,7,8-tetrahydronaphthalene-2-acetic acid, ethyl ester, hydrochloride.

Mass Spectrum (API+): Found MH+ 527. C34H42N2O3 requires 526.

EXAMPLE 3

5-Hydroxy-N-(4-(4-phenylbenzoylamino)butyl)-2-(R,S)-methylamino-1,2,3,4-tetrahydronaphthalene, hydrochloride To a stirred solution of 5-methoxy-N-(4-(4-phenylbenzoylamino)butyl)-2-(R,S)-methylamino-1,2,3,4-tetrahydronaphthalene (0.29 g, 0.66 mmol) in dichloromethane (10 ml) at 0° C., under argon, was added a solution of boron tribromide in dichloromethane 1M; 4 ml; 4 mmol). The reaction mixture was stirred at room temperature for 24 h then poured into a mixture of ice (50 g) and 0.880 ammonia (50 ml). Resultant was extracted with dichloromethane (3×30 ml) and the combined extracts were dried ($Na_2SO_4$) and evaporated in vacuo to give an oil (0.50 g). Chromatography on neutral alumina eluting with dichloromethane containing 0–0.25% methanol gave an oil which was treated with ethereal HCl and dichloromethane to afford the title compound as a white solid (0.3 g, 98%).

FAB Mass Spectrum: found $MH^+$429.2539.$C_{28}H_{32}N_2O_2H$ requires 429.2542

The following compounds were prepared in a similar manner to Example 3:

(a) 7-Hydroxy-N-(4-(4-plenylbenzoylamino)butyl)-2-(R,S)-methylamino-1,2,3,4-tetrahydronaphthalene, hydrochloride Mass spectrum: found $M^+$ 428.2458. $C_{28}H_{32}N_2O_2$ requires 428.2464.

(b) 7-Hydroxy-N-(4-(2-methyl-4-phenyl)benzoylamino) butyl-2-(R,S)-methylamino-1,2,3,4-tetrahydronaphthalene, hydrochloride Mass spectrum: found $M^+$ 442.2634. $C_{29}H_{34}N_2O_2$ requires 442.2621.

(c) 7-Hydroxy-N-(4-(3-methyl-4-phenyl)benzoylamino) butyl-2-(R,S)-methylamino-1,2,3,4-tetrahydronaphthalene, hydrochloride Mass spectrum: found $M^+$ 442.2634. $C_{29}H_{34}N_2O_2$ requires 442.2621.

(d) 7-Hydroxy-N-(4-(4-(4-(1,2,3-thiadiazolyl))benzoyl-amino)butyl)-2-(R,S)-methylamino-1,2,3,4-tetrahydronaphthalene, hydrochloride Mass spectrum: found $M^+$ 436.1927. $C_{24}H_{28}N_4O_2S$ requires 436.1934.

(e) 7-Hydroxy-N-(4-(4-(4-acetyl)phenyl)benzoylamino) butyl-2-(R,S)-methylamino-1,2,3,4-tetrahydronaphthalene, hydrochloride Mass spectrum: found $M^+$ 470.2575. $C_{30}H_{34}N_2O_3$ requires 470.2569.

(f) 7-Hydroxy-N-(4-(2-naphthoyl)amino)butyl-2-(R,S)-methylamino-1,2,3,4-tetrahydronaphthalene $^1$H NMR (CDCl$_3$) δ: 1.77 (5H, m), 2.17 (1H, m), 2.45 (3H, s), 2.60–2.95 (6H, m), 3.13 (1H, m), 3.52 (2H, m), 3.80 (1H, br s), 6.58 (1H, d, J=3 Hz), 6.66 (1H, dd, J=9, 3 Hz), 6.88 (1H, d, J=9 Hz), 7.53 (2H, m), 7.75–8.00 (5H, m), 8.40 (1H, br s).

(g) 6-Hydroxy-N-(4-(4-phenylbenzoylamino)butyl)-3-(R,S)-methylamino-3,4-dihydro-2H-benzo[b]pyran $^1$H NMR (DMSO-d$_6$) δ: 1.62 (4H, m), 2.50 (3H, s), 2.70 (2H, br m), 3.10 (2H, br m), 3.40 (3H, br m), 4.11 (1H, m), 4.78 (1H, m), 6.53 (2H, m), 6.63 (1H, d, J=9 Hz), 7.38–7.57 (3H, m), 7.77 (4H, m), 7.98 (2H, d, J=9 Hz), 8.60 (1H, br m), 9.00 (1H, br s).

(h) 7-Hydroxy-N-(4-(4-(4-methanesulfonyl)phenyl) benzoyl-amino)butyl-2-(R,S)-methylamino-1,2,3,4-tetrahydronaphthalene, hydrochloride.

$^1$H NMR (DMSO-d$_6$) δ: 1.63 (2H, m), 1.78 (3H, m), 2.25 (1H, m), 2.65–2.85 (5H, m), 2.90–3.20 (3H, m), 3.27 (3H, s), 3.30–3.45 (3H, m), 3.59 (1H, m), 6.56 (2H, m), 6.90 (1H, d, J=9 Hz), 7.86 (2H, d, J=9 Hz), 8.01 (6H, m), 8.70 (1H, br t), 9.23 (1H, br s), 10.42 (1H, br s).

(i) 7-Hydroxy-N-(4-(4-(4-(3-(5-methyl-(1,2,4-oxadiazolyl)))-2-methylphenyl)benzoylamino)butyl)-2-(R,S)-methylamino-1,2,3,4-tetrahydronaphthalene, hydrochloride $^1$H NMR (CD$_3$OD) δ: 1.74–2.00 (5H, m), 2.30 (4H, m), 2.67 (3H, s), 2.79–2.98 (5H, m), 3.08 (2H, m), 3.20–3.58 (4H, m), 3.70 (1H, m), 6.60 (2H, m), 6.93 (1H, d, J=9 Hz), 7.35 (1H, d, J=9 Hz), 7.46 (2H, d, J=9 Hz), 7.94 (4H, m).

(j) 5-Hydroxy-N-(4-(4-phenylbenzoylamino)butyl)-2-(R,S)-propylamino-1,2,3,4-tetrahydronaphthalene, hydrochloride $^1$H NMR (DMSO-d$_6$) δ: 0.93 (3H, t, J=7 Hz), 1.63 (2H, m), 1.77 (3H, m), 2.28 (1H, m), 2.40–2.58 (5H, m), 2.91 (1H, dd, J=17, 4 Hz), 3.05 (2H, m), 3.17 (2H, m), 3.34 (2H, m), 3.61 (1H, m), 6.56 (1H, d, J=9 Hz), 6.64 (1H, d, J=9 Hz), 6.95 (1H, t, J=9 Hz), 7.41 (1H, m), 7.50 (2H, t, J=9 Hz), 7.74 (4H, m), 7.95 (2H, d, J=9 Hz), 8.61 (1H, t, J=4 Hz), 9.40 (1H, s), 9.58 (1H, br s).

(k) 8-Hydroxy-N-(4-(4-phenylbenzoylamino)butyl)-3-(R,S)-propylamino-3,4-dihydro-2H-benzopyran, hydrochloride Mass spectrum: found $M^+$ 458.2584. $C_{29}H_{34}N_2O_3$ requires 458.2570

(l) cis-5-Hydroxy-1-methyl-N-(4-(4-phenylbenzoylamino) butyl)-2-(R,S)-propylamino-1,2,3,4-tetrahydronaphthalene, hydrochloride Mass spectrum: found $M^+$ 470.2937. $C_3H_{38}N_2O_2$ requires 470.2933.

EXAMPLE 4

(R or S)-5-Methoxy-N-(4-(4-phenylbenzoylamino) butyl)-2-methylamino-1,2,3,4-tetrahydronaphthalene, hydrochloride (Enantiomer A)

Prepared from (R or S)-5-methoxy-2-methylamino-1,2,3,4-tetrahydronaphthalene (Enantiomer A), by the method of Example 1 in 89% yield.

Mass spectrum: found $M^+$ 442.2621. $C_{29}H_{34}N_2O_2$ requires 442.2620.

HPLC: enantiomeric purity 95.7% (Chiralpak AD, 92:8 hexane-ethanol containing 0.1% diethylamine).

EXAMPLE 5

(R or S)-5-Hydroxy-N-(4-(4-phenylbenzoylamino) butyl)-2-methylamino-1,2,3,4-tetrahydronaphthalene, oxalate (Enantiomer A)

Prepared from (R or S)-5-methoxy-N-(4-(4-phenylbenzoylamino)-butyl)-2-methylamino-1,2,3,4-tetrahydronaphthalene (Enantiomer A), by the method of Example 3 in 59% yield. The compound was purified as the oxalate salt.

$^1$H NMR (CDCl$_3$) δ: 1.78 (2H, m), 1.92 (2H, m), 2.36 (1H, m), 2.58 (2H, m), 2.80 (3H, s), 3.04 (3H, m), 3.22 (2H, m), 3.48 (2H, m), 3.61 (1H, m), 4.90 (2H, br s), 6.55 (1H, d, J=8 Hz), 6.75 (1H, d, J=8 Hz), 6.93 (1H, t, J=8 Hz), 7.38 (1H, m), 7.45 (2H, m), 7.62 (4H, m), 7.97 (2H, d, J=8 Hz), 8.10 (1H, br t), 12.40 (1H, br s).

HPLC: enantiomer purity 95.5% (Chiralpak AD, hexane+ 0.1% diethylamine, ethanol+0.1% diethylamine, 80/20 gradient).

EXAMPLE 6

(R or S)-5-Methoxy-N-(4-(4-phenylbenzoylamino)butyl)-2-methylamino-1,2,3,4-tetrahydronaphthalene, hydrochloride (Enantiomer B)

Prepared from (R or S)-5-methoxy-2-methylamino-1,2,3,4-tetrahydronaphthalene (Enantiomer B), by the method of Example 1 in 53% yield.

Mass spectrum: found $M^+$ 442.2617. $C_{29}H_{34}N_2O_2$ requires 442.2620

HPLC: enantiomeric purity 86.0% (Chiralpak AD, 92:8 hexane-ethanol containing 0.1% diethylamine).

EXAMPLE 7

(R or S)-5-Hydroxy-N-(4-(4-phenylbenzoylamino)butyl)-2-methylamino-1,2,3,4-tetrahydronaphthalene, hydrobromide (Enantiomer B).

Prepared from (R or S)-5-methoxy-N-(4-(4-phenylbenzoylamino)-butyl)-2-methylamino-1,2,3,4-tetrahydronaphthalene (Enantiomer B), by the method of Example 3, in 60% yield. The compound was purified as the hydrobromide salt.

Mass spectrum: found $M^+$ 428.2469. $C_{28}H_{32}N_2O_2$ requires 428.2464.

HPLC: enantiomeric purity 85.9% (Chiralpak AD, 80:20 hexane-ethanol containing 0.1% diethylamine).

EXAMPLE 8

2-(4-(4-Phenylbenzoylamino)butylaminoindane, hydrochloride

Prepared from 2-aminoindane and 4-(4-phenylbenzoylamino)buty-raldehyde by the method of Example 1 in 80% yield.

Mass spectrum: found $M^+$ 384.2202. $C_{26}H_{28}N_2O$ requires 384.2202.

EXAMPLE 9

N-(4-(4-Phenylbenzoylamino)butyl)-2-methylaminoindane, hydrochloride

A mixture of 2-(4-(4-phenylbenzoylamino)butylaminoindane (0.25 g, 0.65 mmol) and paraformaldehyde (0.0 g, 0.65 mmol) in dichloroethane (20 ml) was treated with sodium tris-acetoxyborohydride (0.21 g, 0.97 mmol) and acetic acid (0.037 ml; 0.65 mmol). The mixture was heated at reflux for 8 h, cooled, then partitioned between saturated aqueous $NaHCO_3$ (100 ml) and dichloromethane (3×50 ml). The combined organic extracts were dried ($Na_2SO_4$) and evaporated in vacuo to give an oil (0.31 g). Chromatography on silica using 50–100% ethyl acetate-hexane gradient elution gave an oil (0.11 g, 42%), which was treated with ethereal HCl and dichloromethane to afford the title compound.

Mass spectrum: found $M^+$ 398.2340. $C_{27}H_{30}N_2O$ requires 398.2358.

EXAMPLE 10

7-Methoxy-N-(4-(2-(9-oxofluorenyl)carboxamido)butyl-2-(R,S)-methylamino-1,2,3,4-tetrahydronaphthalene A mixture of N-(4-aminobutyl)-7-methoxy-2-(R,S)-methylamino-1,2,3,4-tetrahydronaphthalene (0.86 g, 3.24 mmol), diisopropylethylamine (0.50 ml; 3.5 mmol) and 2-(9-oxofluorenyl)carbonyl chloride (0.78 g, 3.21 mmol) in dichloromethane (4 ml) was stirred at room tempertaure for 1.5 h, then treated with saturated aqueous $K_2CO_3$. The organic phase was separated, then dried ($NaSO_4$) and evaporated in vacuo. Chromatography of the residue on silica using 5% methanol-dichloromethane elution gave the title compound (0.82 g, 55%) as a pale yellow solid, mp 91–93° C.

$^1H$ NMR ($CDCl_3$) δ: 1.72 (5H, m), 2.05 (1H, m), 2.35 (3H, m), 2.61 (2H, m), 2.82 (4H, m), 2.95 (1H, m), 3.48 (2H, m), 3.74 (3H, s), 6.58 (1H, d, J=3 Hz), 6.64 (1H, dd, J=9, 3 Hz), 6.95 (1H, d, J=9 Hz), 7.34 (1H, dt, J=9, 3 Hz), 7.49–7.26 (5H, m), 7.97 (1H, d, J=2 Hz), 8.06 (1H, dd, J=9, 3 Hz).

The following compounds were prepared in a similar manner to Example 10:

(a) 7-Methoxy-N-(4-(3-methyl-4-phenyl)benzoylamino)butyl-2-(R,S)-methylamino-1,2,3,4-tetrahydronaphthalene Mass spectrum: found $M^+$ 456.2763. $C_{30}N_{36}N_2O_2$ requires 456.2777.

(b) 7-Methoxy-N-(4-(2-methyl-4-phenyl)benzoylamino)butyl-2-(R,S)-methylamino-1,2,3,4-tetrahydronaphthalene Mass spectrum: found $M^+$ 456.2768. $C_{30}H_{36}N_2O_2$ requires 456.2777.

(c) 7-Methoxy-N-(4-(4-(1,2,3-thiadiazolyl))benzoylamino)-butyl)-2-(R,S)-methylamino-1,2,3,4-tetrahydronaphthalene Mass spectrum: found $M^+$ 450.2074. $C_{25}H_{30}N_4O_2$ requires 450.2090.

(d) 7-Methoxy-N-(4-(4-(4-acetyl)phenyl)benzoylamino)butyl-2-(R,S)-methylamino-1,2,3,4-tetrahydronaphthalene Mass spectrum: found $M^+$ 484.2715. $C_{31}H_{36}N_2O_3$ requires 484.2726.

(e) 7-Methoxy-N-(4-(4-(4-(3-(5-methyl-(1,2,4-oxadiazolyl)))-2-methylphenyl)benzoylamino)-2-(R,S)-methylamino-1,2,3,4-tetrahydronaphthalene Mass spectrum: found $M^+$ 538.2932. $C_{33}H_{38}N_4O_3$ requires 538.2944.

(f) N-(4-(4-phenylbenzoylamino)butyl)-2-(R,S)-propylamino-1,2,3,4-tetrahydronaphthalene, hydrochloride Mass spectrum: found $M^+$ 440.2835. $C_{30}H_{36}N_2O$ requires 440.2827.

EXAMPLE 11

7-Methoxy-N-(4-(2-naphthoyl)amino)butyl-2-(R,S)-methyl-amino-1,2,3,4-tetrahydronaphthalene, hydrochloride A solution of N-(4-aminobutyl)-7-methoxy-2-(R,S)-methylamino-1,2,3,4-tetrahydronaphthalene (0.95 g, 3.63 mmol) in DMF (2 ml) was added to a solution of 2-naphthoic acid (0.62 g, 3.63 mmol), 1-hydroxybenzotriazole (0.49 g, 3.63 mmol) and 1-(3-dimethylamino-propyl)-3-ethylcarbodiimide hydrochloride (0.70 g, 3.63 mmol) in DMF (45 ml). The mixture was stirred for 18 h then treated with saturated aqueous $K_2CO_3$ (50 ml) and ethyl acetate (50 ml). The organic phase was separated and the aqueous phase further extracted with ethyl acetate (2×50 ml). The combined extracts were washed with water (3×100 ml) brine (100 ml), dried ($Na_2SO_4$) and evaporated in vacuo to give an oil (1.44 g). Chromatography on silica using 5% methanol dichloromethane elution gave an oil which was treated with ethereal HCl to give the title compound (0.90 g, 70%).

$^1H$ NMR ($CDCl_3$) δ: 1.72 (5H, m), 2.02 (1H, m), 2.32 (3H, s), 2.62 (2H, m), 2.82 (4H, m), 2.94 (1H, m), 3.52 (2H, m), 3.75 (3H, m), 6.57 (1H, d, J=3 Hz), 6.68 (1H, d=9, 3 Hz), 6.95 (1H, d, J=9 Hz), 7.40 (1H, br t), 7.53 (2H, m), 7.86 (4H, m), 8.30 (1H, s). (Free base).

The following compounds were prepared in a similar manner to Example 11:

(a) 5-Methoxy-N-(4-(4-(2-pyrimidyl)benzoylamino)butyl-2-(R,S)-propylamino-1,2,3,4-tetrahydronaphthalene, dihydrochloride $^1$H NMR (DMSO-$d_6$) δ: 0.92 (3H, t, J=7 Hz), 1.65 (2H, m), 1.80 (6H, m), 2.33 (1H, m), 2.53 (1H, m), 3.11 (6H, m), 3.28 (1H, m), 3.37 (2H, m), 3.60 (1H, m), 3.76 (3H, s) 6.70 (1H, d, J=9 Hz), 6.80 (1H, d, J=9 Hz), 7.13 (1H, t, J=9 Hz), 7.50 (1H, t, J=5 Hz), 8.01 (2H, d, J=9 Hz), 8.46 (2H, d, J=9 Hz), 8.70 (1H, m), 8.95 (2H, d, J=5 Hz), 10.04 (1H, br s).

(b) 5-Methoxy-N-(4-(4-(3-pyridyl)benzoylamino)butyl)-2-(R,S)-propylamino-1,2,3,4-tetrahydronaphthalene, dihydrochloride Mass spectrum (API$^+$): 472 (MH$^+$, 100%). $C_{30}H_{37}N_3O_2$ requires 471.

(c) 5-Methoxy-N-(4-(4-(4-pyridyl)benzoylamino)butyl)-2-(R,S)-propylamino-1,2,3,4-tetrahydronaphthalene, dihydrochloride Mass spectrum (API$^+$): 472 (MH$^+$, 100%). $C_{30}H_{37}N_3O_2$ requires 471.

(d) 5-Methoxy-N-(4-(4-(5-pyrimidyl)benzoylamino)butyl)-2-(R,S)-propylamino-1,2,3,4-tetrahydronaphthalene, dihydrochloride Mass spectrum (API$^+$): 473 (MH$^+$, 100%). $C_{29}H_{36}N_4O_2$ requires 472.

(e) 5-Methoxy-N-(4-(4-(4-triazolyl)benzoylamino)butyl)-2-(R,S)-propylamino-1,2,3,4-tetrahydronaphthalene, dihydrochloride Mass spectrum (API$^+$): 462 (MH$^+$, 55%). $C_{27}H_{35}N_5O_2$ requires 461.

(f) 5-Methoxy-N-(4-(4-(1-triazolyl)benzoylamino)butyl)-2-(R,S)-propylamino-1,2,3,4-tetrahydronaphthalene, dihydrochloride Mass spectrum (API$^+$): 462 (MH$^+$, 100%). $C_{27}H_{35}N_5O_2$ requires 461.

(g) 5-Methoxy-N-(4-(4-pyridazylbenzoylamino)butyl)-2-(R,S)-propylamino-1,2,3,4-tetrahydronaphthalene, dihydrochloride Mass spectrum (API$^+$): 473 (MH$^+$, 100%). $C_{29}H_{36}N_4O_2$ requires 472.

EXAMPLE 12

7-Hydroxy-N-(4-(4-(4-methoxy)phenyl) benzoylamino)butyl-2-(R,S)-methylamino-1,2,3,4-tetrahydronaphthalene, hydrochloride A mixture of 7-hydroxy-N-(4-(4-bromobenzoyl)amino) butyl-2-(R,S)-methylamino-1,2,3,4-tetrahydronaphthalene (0.43 g, 1.0 mmol), 4-methoxyphenylboronic acid (0.20 g, 1.21 mmol), dimethoxyethane (5.4 ml) and aqueous $Na_2CO_3$ (2M; 1.7 ml) was treated with tetrakis-triphenylphosphinepalladium (0) (0.05 g) then heated at reflux under argon for 2 h. The mixture was cooled, then partitioned between water (100 ml) and ethyl acetate (3×50 ml). The combined organic extracts were dried ($Na_2SO_4$) and evaporated in vacuo to give an oil (0.57 g). Chromatography on alumina using 2–4% methanol-dichloromethane gradient elution gave an oil (0.17 g). Treatment with HCl-ether gave the title compound (0.098 g, 21%) as a yellow powder, mp 124–5° C.

$^1$H NMR (CDCl$_3$) δ: 1.66 (5H, m), 1.99 (1H, m), 2.30 (3H, s), 2.55 (2H, m), 2.62–2.91 (5H, m), 3.47 (2H, m), 3.85 (3H, s), 6.50 (1H, d, J=3 Hz), 6.61 (1H, dd, J=9, 3 Hz), 6.89 (1H, d, J=9 Hz), 6.97 (2H, d, J=9 Hz), 7.15 (1H, br t), 7.54 (4H, t, J=9 Hz), 7.78 (2H, d, J=9 Hz) (Free base).

The following compounds were prepared in a similar manner to Example 12:

(a) 7-Hydroxy-N-(4-(4-(4-pyridyl)benzoyl)amino)butyl-2-(R,S)-methylamino-1,2,3,4-tetrahydronaphthalene, hydrochloride $^1$H NMR (CD$_3$OD) δ: 1.60–2.02 (5H, m), 2.26 (1H, m), 2.79–2.96 (5H, m), 3.10 ) 2H, m), 3.20–3.58 (4H, m), 3.69 (1H, m), 6.57 (2H, m), 6.92 (1H, d, J=9 Hz), 8.08 (4H, s), 8.46 (2H, d, J=7 Hz), 8.93 (2H, d, J=7 Hz).

(b) 7-Hydroxy-N-(4-(4-(3-pyridyl)benzoyl)amino)butyl-2-(R,S)-methylamino-1,2,3,4-tetrahydronaphthalene, dihydrochloride Mass spectrum: found M$^+$ 429.2409. $C_{27}H_{31}N_3O_2$ requires 429.2416.

(c) 7-Hydroxy-N-(4-(4-(2-pyridyl)benzoyl)amino)butyl-2-(R,S)-methylamino-1,2,3,4-tetrahydronaphthalene, dihydrochloride $^1$H NMR (CD$_3$OD) δ: 1.79 (2H, m), 1.90 (3H, m), 2.30 (1H, m), 2.91 (5H, m), 3.07 (2H, m), 3.29 (1H, m), 3.42 (1H, m), 3.52 (2H, m), 3.69 (1H, m), 6.57 (2H, m), 6.92 (1H, d, J=9 Hz), 8.05 (3H, m), 8.14 (2H, m), 8.43 (1H, d, J=8 Hz), 8.66 (1H, t, J=8 Hz), 8.88 (1H, d, J=5 Hz).

(d) N-(4-(4-(4-Pyridyl)benzoyl)amino)butyl-2-(R,S)-propylamino-1,2,3,4-tetrahydronaphthalene, dihydrochloride Mass spectrum: found M$^+$ 441.2774. $C_{29}H_{35}N_3O$ requires 441.2780.

EXAMPLE 13

7-Hydroxy-N-(4-(2-(9-oxofluorenyl))carboxamido) butyl-2-(R,S)-methylamino-1,2,3,4-tetrahydronaphthalene Prepared from N-(4-aminobutyl)-7-hydroxy-3-(R,S)-methylamino-1,2,3,4-tetrahydronaphthalene and 2-(9-oxofluorenyl)carbonyl chloride by a method similar to that of Example 10.

$^1$H NMR (CDCl$_3$) δ: 1.75 (5H, m), 2.16 (1H, m), 2.49 (3H, s), 2.67–2.95 (6H, m), 3.12 (1H, m), 3.48 (2H, m), 6.60 (2H, m), 6.86 (1H, d, J=9 Hz), 7.35 (1H, m), 7.45–7.68 (4H, m), 8.09 (3H, m).

EXAMPLE 14

7-Methoxy-N-(4-(4-(4-methansulfonyl)phenyl) benzoyl-amino)butyl-2-(R,S)-methylamino-1,2,3,4-tetrahydronaphthalene A mixture of 7-methoxy-N-(4-(4-tributylstannyl)benzoyl-amino)butyl-2-(R,S)-methylamino-1,2,3,4-tetrahydronaphthalene (0.70 g, 1.1 mmol), 1-bromo-4-methanesulfonylbenzene (0.25 g, 1.06 mmol), xylene (7 ml) and tetrakis-triphenylphosphinepalladium (0) (0.12 g) was heated at reflux under argon for 3.5 h. The mixture was cooled then partitioned between water (100 ml) and ethyl acetate (3×50 ml). The combined organic extracts were dried ($Na_2SO_4$) and evaporated in vacuo to an oil. Flash chromatography on silica with 2–10% methanol-dichloromethane gradient elution gave the title compound (0.22 g, 40%) as a foam.

$^1$H NMR (CDCl$_3$) δ: 1.75 (5H, m), 2.09 (1H, m), 2.42 (3H, s), 2.65–2.90 (6H, m), 3.05 (1H, m), 3.10 (3H, s), 3.52 (2H, m), 3.76 (3H, m), 6.58 (1H, d, J=3 Hz), 6.68 (1H, dd, J=9, 3 Hz), 6.96 (1H, d, J=9 Hz), 7.46 (1H, br m), 7.65 (2H, d, J=9 Hz), 7.76 (2H, d, J=9 Hz), 7.93 (2H, d, J=9 Hz), 8.03 (2H, d, J=9 Hz).

EXAMPLE 15

N-(4-(4-Phenylbenzoylamino)butyl)-2-(R,S)-propylamino-5-trifluoromethanesulfonyloxy-1,2,3,4-tetrahydronaphthalene, hydrochloride To a stirred solution of 5-hydroxy-N-(4-(4-phenylbenzoylamino)-butyl)-2-(R,S)-propylamino-1,2,3,4-tetrahydronaphthalene (1.0 g, 2.2 mmol) in pyridine (10 ml) at 0° C. under argon was added trifluoromethanesulfonic anhydride (0.51 ml; 0.85 g, 3 mmol). The mixture was stirred at 0° C. for 2 h, then poured into aqueous copper (II) sulfate (20%; 150 ml) and extracted with ethyl acetate (150 ml). The organic phase was washed with aqueous copper (II) sulfate (5%; 100 ml) and brine (50 ml) then dried ($Na_2SO_4$) and evaporated in vacuo to give a foam (1.45 g). Chromatography on alumina with 10–100% ethyl acetate-hexane gradient elution gave the free base of the title compound (0.96 g, 74%). A sample was treated with HCl-ether to give the title compound.

Mass spectrum: found $M^+$ 588.2259. $C_{31}H_{35}F_3N_2O_4S$ requires 588.2266.

The following compound was prepared in a similar manner to Example 15:
(a) N-(4-(4-Phenylbenzoylamino)butyl)-3-(R,S)-propylamino-8-trifluoromethanesulfonyloxy-3,4dihydro-2H-benzopyran, hydrochloride Mass spectrum: found $M^+$ 590.2042. $C_{30}H_{33}F_3N_2O_5S$ requires 590.2063
(b) cis-1-Methyl-N-(4-(4-phenylbenzoylamino)butyl)-2-(R,S)-propylamino-5-tritluoromethanesulfonyloxy-1,2,3,4-tetrahydronapthalene, hydrochloride Mass spectrum: found $M^+$ 602.2435. $C_{32}H_{37}F_3N_2O_4S$ requires 602.2437.

EXAMPLE 16

5-Cyclopropylmethoxy-N-(4-(4-phenylbenzoylanino)butyl)-2-(R,S)-propylamino-1,2,3,4-tetrahydronaphthalene, hydrochloride A mixture of 5-hydroxy-N-(4-(4-phenylbenzoylamino)butyl)-2-(R,S)-propylamino-1,2,3,4-tetrahydronaphthalene (0.10 g, 0.22 mmol), anhydrous potassium carbonate (0.50 g, 3.6 mmol) and (bromomethyl)cyclopropane (0.16 ml; 0.21 g, 1.5 mmol) in dry dimethylformamide (3 ml) was stirred at 70° C. under argon for 6 h. Excess solvent was evaporated in vacuo, and the residue was partitioned between water (150 ml) and ethyl acetate (3×30 ml). The combined organic extracts were dried ($Na_2SO_4$) and evaporated in vacuo to give an oil. Chromatography on alumina with 1:1 ether-hexane elution gave the free base of the title compound as an oil (0.072 g, 64%). Treatment with HCl-ether gave the title compound.

$^1$H NMR (DMSO-$d_6$) δ: 0.30 (2H, m), 0.54 (2H, m), 0.93 (3H, t, J=7 Hz), 1.20 (1H, m), 1.63 (2H, m), 1.76 (3H, m), 2.29 (1H, m), 2.45–2.62 (2H, m), 2.93–3.45 (10H, m), 3.63 (1H, m), 3.81 (2H, d, J=7 Hz), 6.70 (1H, d, J=9 Hz), 6.75 (1H, d, J=9 Hz), 7.09 (1H, t, J=9 Hz), 7.41 (1H, m), 7.50 (2H, t, J=9 Hz), 7.74 (4H, m), 7.94 (2H, d, J=9 Hz), 8.59 (1H, t, J=4 Hz), 9.48 (1H, br s).

mp 101–3° C.

IR $v_{c=o}$ 1644

Mass spectrum: found $M^+$ 510.3238. $C_{34}H_{42}N_2O_2$ requires 510.3246.

EXAMPLE 17

5-Methanesulfonyloxy-N-(4-(4-phenylbenzoylamino)butyl)-2-(R,S)-propylamino-1,2,3,4-tetrahydronaphthalene, hydrochloride To a stirred solution of 5-hydroxy-N-(4-(4-phenylbenzoylamino)butyl)-2-(R,S)-propylamino-1,2,3,4-tetrahydronaphthalene (0.59 g, 1.3 mmol) and triethylamine (0.22 ml; 0.157 g, 1.55 mmol) in dichloromethane (20 ml) at room temperature was added methanesulfonyl chloride (0.12 ml; 0.178 g, 1.55 mmol). The mixture was stirred for 2 h, then partitioned between saturated aqueous $NaHCO_3$ (50 ml) and dichloromethane (3×50 ml). The combined organic extracts were dried ($Na_2SO_4$) then evaporated in vacuo to give an oil (0.53 g). Chromatography on silica gel using 20–100% EtOAc-hexane gradient elution gave an oil (0.35 g, 52%). Conversion to the hydrochloride salt gave the title compound.

Mass spectrum: found $M^+$ 534.2532. $C_{31}H_{38}N_2O_4S$ requires 534.2552.

The following compound was prepared in a manner similar to Example 17:
(a) N-(4-(4-Phenylbenzoylamino)butyl)-3-(R,S)-propylamino-8-methanesulfonyloxy-3,4-dihydro-2H-benzo[b]pyran, hydrochloride $^1$H NMR (DMSO-$d_6$) δ: 0.88 (3H, t, J=7 Hz), 1.58 (2H, m), 1.75 (4H, m), 3.05–3.30 (8H, m), 3.30 (3H, s), 3.95 (1H, br s), 4.43 (1H, m), 4.62 (1H, m), 6.98 (1H, m), 7.17 (2H, m), 7.39 (1H, m), 7.48 (2H, m), 7.30 (4H, m), 7.93 (2H, d, J=9 Hz), 8.60 (1H, m), 10.55 (1H, br s).

EXAMPLE 18

7-Cyano-N-(4-(4-phenylbenzoylamino)butyl)-2-(R,S)-propylamino-1,2,3,4-tetrahydronaphthalene, hydrochloride A mixture of 7-bromo-N-(4-(4-phenylbenzoylamino)butyl-2-(R,S)-propylamino-1,2,3,4-tetrahydronaphthalene (1.39 g, 2.65 mmol), zinc cyanide (0.51 g, 4.30 mmol), tetrakis-triphenylphosphinepalladium (0) and dimethylformamide (25 ml) was heated to 100–130° C. for 2 h. The mixture was cooled, then partitioned between dilute aqueous ammonia (200 ml) and ethyl acetate (200 ml). The organic phase was washed with water (2×200 ml), dried ($Na_2SO_4$) then evaporated in vacuo to give an oil (1.49 g). Chromatography on silica gel with 10–100% ethyl acetate-hexane gradient elution gave an oil (1.0 g, 87%). Conversion to the hydrochloride salt gave the title compound.

Mass spectrum: found $M^+$ 465.2775. $C_{31}H_{35}N_3O$ requires 465.2781.

The following compounds were prepared in a manner similar to Example 18:
(a) 5-Cyano-N-(4-(4-phenylbenzoylamino)butyl)-2-(R,S)-propylamino-1,2,3,4-tetrahydronaphthalene, hydrochloride FAB Mass spectrum: found $MH^+$ 466.2890. $C_{31}H_{35}N_3OH$ requires 466.2858.
(b) 6-Cyano-N-(4-(4-phenylbenzoylamino)butyl)-2-(R,S)-propylamino-1,2,3,4-tetrahydronaphthalene, hydrochloride $^1$H NMR (DMSO-$d_6$) δ: 0.95 (3H, t, J=7 Hz), 1.59 (2H, m), 1.61–1.95 (5H, m), 2.37 (1H, m), 2.82–3.29 (9H, m), 3.65–3.75 (1H, m), 7.30–7.79 (10H, m), 7.95 (2H, d, J=9 Hz), 8.65 (1H, m), 10.45 (1H, br s).

EXAMPLE 19

7-(R,S)-(N-(4-(4-Phenylbenzoylamino)butyl) propylamino)-5,6,7,8-tetrahydronaphthalene-2-carboxamide To a solution of 7-cyano-N-(4-(4-phenylbenzoylamino) butyl)-2-(R,S)-propylamino-1,2,3,4-tetrahydronaphthalene (0.983 g, 2.11 mmol) in dimethyl sulfoxide (4 ml) at 15° C. was added a solution of hydrogen peroxide in water (27.5% w/v; 0.26 ml; 2.12 mmol) followed by anhydrous potassium carbonate (0.42 g, 3.06 mmol). The mixture was stirred for 6 h at room temperature, then poured into water (100 ml) and the resulting solid filtered off to give the title compound (0.84 g, 82%).

$^1$H NMR (CDCl$_3$) δ: 0.88 (3H, t, J=7 Hz), 1.47 (2H, q, J=7 Hz), 1.50–1.82 (5H, m), 2.02 (1H, m), 2.48 (2H, t, J=7 Hz), 2.57 (2H, t, J=7 Hz), 2.72–3.04 (5H, m), 3.50 (2H, q, J=7 Hz), 5.50 (1H, br s), 6.05 (1H, br s), 6.45 (1H, br m), 7.12 (1H, d, J=9 Hz), 7.35–7.69 (9H, m), 7.83 (2H, d, J=9 Hz).

The following compounds were prepared in a manner similar to Example 19:

(a) 6-(R,S)-(N-(4-(4-Phenylbenzoylamino)butyl)propylamino)-5,6,7,8-tetrahydronaphthalene-1-carboxamide, hydrochloride Mass spectrum: found M$^+$ 483.2875. C$_{31}$H$_{37}$N$_3$O$_2$ requires 483.2886.

(b) 6-(R,S)-(N-(4-(4-Phenylbenzoylamino)butyl)propylamino)-5,6,7,8-tetrahydronapthalene-2-carboxamide $^1$H NMR (DMSO-d$_6$) δ: 0.95 (3H, t, J=7 Hz), 1.36–1.60 (7H, m), 1.95 (1H, m), 2.46 (4H, m), 2.68–2.95 (5H, m), 3.30 (3H, m), 7.18 (1H, d, J=9 Hz), 7.19 (1H, br s), 7.31–7.49 (5H, m), 7.72 (3H, m), 7.82 (1H, s), 7.9 (2H, d, J=9 Hz), 8.5 (1H, m).

EXAMPLE 20

N,N-Dimethyl-(7-(R,S)-(N-(4-(4-phenylbenzoylamino)butyl)propylamino)-5,6,7,8-tetrahydronaphthalene)-2-carboxamide, hydrochloride To a stirred suspension of 7-(R,S)-(N-(4-(4-phenylbenzoylamino)butyl)propylamino)-5,6,7,8-tetrahydronaphthalene-2-carboxamide (0.58 g, 1.2 mmol) in acetonitrile (5 ml) was added nitrosonium tetrafluoroborate (0.58 g, 5.0 mmol) with ice cooling. The mixture was stirred at room temperature for 18 h then poured into 5N hydrochloric acid (100 ml), and extracted with methanol-dichloromethane (1:10; 5×100 ml). The combined organic extracts were dried (Na$_2$SO$_4$) and evaporated in vacuo to give an oil (0.55 g). A portion of this material (0.27 g) was dissolved in dimethylformamide (8 ml) and treated with 1-ethyl-3-(3-dimethylaminopropyl)carbodiimide (0.108 g, 0.558 mmol), 1-hydroxybenzotriazole (0.086 g, 0.558 mmol) and dimethylamine (40% w/w aqueous solution; 0.21 ml). Resulting solution was stirred at room temperature for 24 h then evaporated in vacuo. The residue was partitioned between saturated aqueous NaHCO$_3$ (50 ml) and ethyl acetate (70 ml). The organic phase was washed with water (3×50 ml), dried (Na$_2$SO$_4$) and evaporated in vacuo to give an oil (0.19 g). Chromatography on silica gel with 50–100% ethyl acetate-hexane gradient elution gave an oil (0.16 g, 60%). Conversion to the hydrochloride salt gave the title compound.

FAB Mass spectrum: found M$^+$ 512.3269. C$_{33}$H$_{41}$N$_3$O$_2$H requires 512.3277.

The following compounds were prepared in a manner similar to Example 20:

(a) N,N-Dimethyl-(6-(R,S)-(N-(4-(4-phenylbenzoylamino)butyl)propylamino)-5,6,7,8-tetrahydronaphthalene)-2-carboxamide, hydrochloride $^1$H NMR (DMSO-d$_6$) δ: 0.95 (3H, t, J=7 Hz), 1.62–1.98 (8H, m), 2.3–2.43 (1H, m), 2.81–3.00 (6H, s), 3.02–3.48 (10H, m), 7.15 (3H, m), 7.34–7.51 (3H, m), 7.7 (4H, t J=9 Hz), 7.95 (2H, d, J=9 Hz), 8.50 (1H, m), 10.30 (1H, br s)

(b) N-Methyl-(7-(R,S)-(N-(4-(4-phenylbenzoylamino)butyl)propylamino-5,6,7,8-tetrahydronaphthalene)-2-carboxamide, hydrochloride FAB Mass spectrum: found MH$^+$498.3042. C$_{32}$H$_{39}$N$_3$O$_2$H requires 498.3121

EXAMPLE 21

6-Methylsulfonyl-N-(4-(4-phenyibenzoyamino)butyl)-2-(R,S)-propylamino-1,2,3,4-tetrahydronaphthalene, hydrochloride Hydrogen peroxide (27.5% w/v in water; 0.5 ml) was added to an ice cooled solution of 6-Methylthio-N-(4-(4-phenylbenzoylamino)butyl)-2-(R,S)-propylamino-1,2,3,4-tetrahydronaphthalene (0.25 g, 0.50 mmol) in glacial acetic acid (7 ml) and the mixture stirred at room temperature for 18 h. The mixture was added dropwise to aqueous K$_2$CO$_3$ (400 ml) then extracted with ethyl acetate (3×100 ml). The combined extracts were dried (Na$_2$SO$_4$) and evaporated in vacuo to give an oil. Chromatography on silica gel with ethyl acetate-pentane elution gave an oil (0.126 g, 50%). Conversion to the hydrochloride salt gave the title compound.

hu 1H NMR (DMSO-d$_6$) δ: 0.92 (3H, t, J=7 Hz), 1.56–1.70 (2H, m), 1.72–1.98 (5H, m), 2.36 (1H, m), 2.88–3.45 (13H, m), 3.72 (1H, m), 7.41 (2H, t, J=9 Hz), 7.49 (2H, t, J=9 Hz), 7.64–7.82 (6H, m), 7.98 (2H, d, J=9 Hz), 8.65 (1H, m), 10.45 (1H, br s).

We claim:

1. A compound of formula (I):

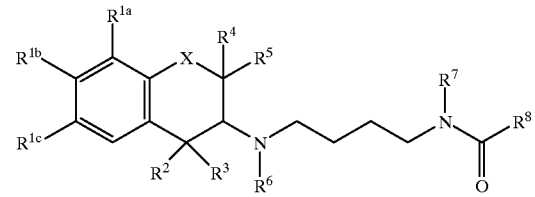

Formula (I)

wherein

X represents a single bond or CR$^9$R$^{10}$ where R$^9$ and R$^{10}$ each independently represent a hydrogen atom or a C$_{1-4}$alkyl group;

R$^{1a}$, R$^{1b}$ and R$^{1c}$ each independently represent a substituent selected from: a hydrogen or halogen atom, a hydroxy, cyano, trifluoromethyl, trifluoromethoxy, trifluoromethanesulfonyloxy, C$_{1-4}$alkyl, C$_{1-4}$alkoxy, C$_{1-4}$alkylthio C$_{1-4}$alkoxyC$_{1-4}$alkyl, C$_{3-6}$cycloalkylC$_{1-4}$alkoxy, C$_{1-4}$alkanoyl, C$_{1-4}$alkoxycarbonyl, C$_{1-4}$alkylsulphonyl, C$_{1-4}$alkylsulphonyloxy, or C$_{1-4}$alkylsulphonylC$_{1-4}$alkyl, arylsulphonylarylsulphonyloxy or arylsulphonylC$_{1-4}$alkyl group, or a group R$^{11}$OCO(CH2)$_p$, R$^{11}$R$^{12}$NCO(CH2)$_p$ or R$^{11}$R$^{12}$NSO$_2$(CH$_2$)$_p$ where each of R$^{11}$ and R$^{12}$ independently represents a hydrogen atom or a C$_{1-4}$alkyl group and p represents zero or an integer from 1 to 4;

R$^2$, R$^3$, R$^4$ and R$^5$ each independently represent a hydrogen atom or a C$_{1-4}$alkyl group;

R$^6$ represents a hydrogen atom or a C$_{1-6}$alkyl, C$_{3-6}$ alkenyl or arylC$_{1-4}$alkyl group;

R$^7$ represents a hydrogen atom or a C$_{1-4}$alkyl group; and

R⁸ represents a group of structure (a), (b) or (c):

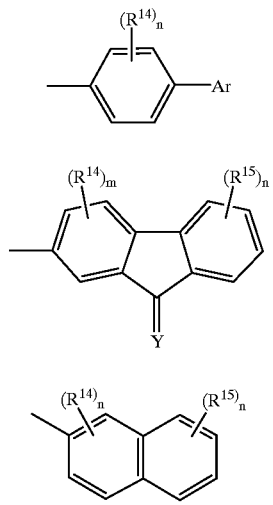

wherein
Ar is furyl, thienyl, pyrrolyl, oxazolyl, thiazolyl, imidazolyl, oxadiazolyl, thiadiazolyl, pyridyl, trizolyl, trizolyl, triazinyl, pyridazyl, pyrimidinyl or pyrazolyl optionally substituted by one or more substituents selected from a hydrogen or halogen atom, or a hydroxy, cyano, nitro, $H_2NCO$, $C_{1-4}$alkyl, $C_{1-4}$alkoxy, $C_{1-4}$alkanoyl or $C_{1-4}$alkylsuslphonyl group; or a group of structure (d):

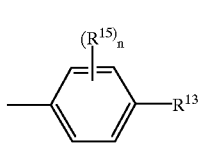

$R^{13}$ represents a hydrogen or halogen atom, or a hydroxy, cyano, nitro, $H_2NCO$, $C_{1-4}$alkyl, $C_{1-4}$alkoxy, $C_{1-4}$alkanoyl or $C_{1-4}$alkylsulphonyl group or is furyl, thienyl, pyrrolyl, oxazolyl, thiazolyl, imidazolyl, oxadiazolyl, thiadiazolyl, pyridyl, triazolyl, triazinyl, pyridazyl, pyrimidinyl or pyrazolyl optionally substituted by one or more substituents selected from a hydrogen or halogen atom, or a hydroxy, cyano, nitro, $H_2NCO$, $C_{1-4}$alkyl, $C_{1-4}$alkoxy, $C_{1-4}$alkanoyl or $C_{1-4}$alkylsuslphonyl group;

each $R^{14}$ and $R^{15}$ independently represents a substituent selected from a hydrogen or halogen atom, or a hydroxy, cyano, nitro, $H_2NCO$, $C_{1-4}$alkyl, $C_{1-4}$alkoxy $C_{1-4}$alkanoyl or $C_{1-4}$alkylsulphonyl, group;

Y represents $H_2$ or an oxygen atom;
n is a number from 1 to 4; and
m is a number from 1 to 3;
or a salt thereof.

2. A compound as claimed in claim 1 wherein $R^{1a}$, $R^{1b}$ and $R^{1c}$ each independently represent a hydrogen or halogen atom, or a hydroxy, cyano, trifluoromethoxy, trifluoromethanesulfonyloxy, $C_{1-4}$alkoxy, $C_{3-6}$cycloalkyl$C_{1-4}$ alkoxy, $C_{1-4}$alkylsulphonyl, $C_{1-4}$alkylsulphonyloxy, $C_{1-4}$alkylsulphonyl$C_{1-4}$alkyl, $C_{1-4}$alkylthio, $R^{11}OCO(CH_2)_p$ or $R^{11}R^{12}NCO(CH2)_p$ group.

3. A compound as claimed in claim 2 wherein $R^{1a}$, $R^{1b}$ and $R^{1c}$ independently represent hydrogen, hydroxy, cyano, or $H_2NCO$.

4. A compound as claimed in claim 2 wherein $R^{1a}$, $R^{1b}$ and $R^{1c}$ independently represent hydrogen, halogen, trifluoromethyl, trifluoromethoxy, $C_{1-4}$alkylsulphonyloxy, trifluoromethanesulphonyloxy, or $R^{11}OCO(CH_2)_p$.

5. A compound as claimed in claim 1 wherein $R^2$ and $R^3$ each represent hydrogen or $C_{1-2}$alkyl.

6. A compound as claimed in claim 1 wherein $R^4$ and $R^5$ each represent hydrogen.

7. A compound as claimed in claim 1 wherein $R^6$ represents methyl, ethyl, propyl or propenyl.

8. A compound as claimed in claim 1 wherein $R^7$ represents a hydrogen atom.

9. A compound of formula (I) which is:
N-(4-(4-phenylbenzoylamino)butyl)-2-(R,S)-methylamino-1,2,3,4-tetrahydronaphthalene;
5-methoxy-N-(4-(4-phenylbenzoylamino)butyl)-2-(R,S)-methyl-amino-1,2,3,4-tetrahydronaphthalene;
5-hydroxy-N-(4-(4-phenylbenzoylamino)butyl)-2-(R,S)-methylamino-1,2,3,4-tetrahydronaphthalene;
7-Methoxy-N-(4-(4-phenylbenzoylamino)butyl)-2-(R,S)-methylamino-1,2,3,4-tetrahydronaphthalene,
7-Hydroxy-N-(4-(4-phenylbenzoylamino)butyl)-2-(R,S)-methylamino-1,2,3,4-tetrahydronaphthalene,
5-Methoxy-N-(4-(4-phenylbenzoylamino)butyl)-2-(R,S)-propylamino-1,2,3,4-tetrahydronaphthalene,
6-Methoxy-N-(4-(4-phenzylbenzoylamino)butyl)-2-(R,S)-methylamino-1,2,3,4-tetrahydronaphthalene,
5-Methoxy-N-(4-(4-phenylbenzoylamino)butyl)-2-(R,S)-ethylamino-1,2,3,4-tetrahydronaphthalene,
7-Methoxy-N-(4-(4-phenylbenzoylamino)butyl-2-(R,S)-propylamino-1,2,3,4-tetrahydronaphthalene,
7-Hydroxy-N-(4-(2-methyl-4-phenyl)benzoylamino)butyl-2-(R,S)-methylamino-1,2,3,4-tetrahydronaphthalene,
7-Hydroxy-N-(4-(3-methyl-4-phenyl)benzoylamino)butyl-2-(R,S)-methylamino-1,2,3,4-tetrahydronaphthalene,
7-Hydroxy-N-(4-(4-(1,2,3-thiadiazolyl))benzoyi-amino) butyl)-2-(R,S)-methylamino-1,2,3,4-tetrahydronaphthalene,
7-Hydroxy-N-(4-(4-(4-acetyl)phenyl)benzoylamino)butyl-2-(R,S)-methylamino-1,2,3,4-tetrahydronaphthalene,
7-Hydroxy-N-(4-(2-naphthoyl)amino)butyl-2-(R,S)-methylamino-1,2,3,4-tetrahydronaphthalene,
7-Hydroxy-N-(4-(4-(4-methanesulfonyl)phenyl)benzoylamino)butyl-2-(R,S)-methylamino-1,2,3,4-tetrahydronaphthalene,
7-Hydroxy-N-(4-(4-(4-(3-(5-methyl-(1,2,4-oxadiazolyl)))-2-methylphenyl)benzoylamino)butyl)-2-(R,S)-methylamino-1,2,3,4-tetrahydronaphthalene,
5-Hydroxy-N-(4-(4-phenylbenzoylamino)butyl)-2-(R,S)-propylamino-1,2,3,4-tetrahydronaphthalene,
(R or S)-5-Methoxy-N-(4-(4-phenylbenzoylamino)butyl)-2-methylamino-1,2,3,4-tetrahydronaphthalene, (Enantiomer A),
(R or S)-5-Hydroxy-N-(4-(4-phenylbenzoylamino)butyl)-2-methylamino-1,2,3,4-tetrahydronaphthalene, (Enantiomer A),
(R or S)-5-Methoxy-N-(4-(4-phenylbenzoylamino)butyl)-2-methylamino-1,2,3,4-tetrahydronaphthalene, (Enantiomer B),
(R or S)-5-Hydroxy-N-(4-(4-phenylbenzoylamino)butyl)-2-methylamino-1,2,3,4-tetrahydronaphthalene, (Enantiomer B),
2-(4-(4-Phenylbenzoylamino)butylaminoindane,
N-(4-(4-Phenylbenzoylamino)butyl)-2-methylaminoindane, 7-Methoxy-N-(4-(2-(9-oxofluorenyl))carboxamido)butyl-2-(R,S)-methylamino-1,2,3,4-tetrahydronaphthalene,
7-Methoxy-N-(4-(3-methyl-4-phenyl)benzoIlamino)butyl-2-(R,S)-methylamino-1,2,3,4-tetrahydronaphthalene,
7-Methoxy-1-(4-(2-methyl-4-phenyl)benzoylamino)butyl-2-(R,S)-methylamino-1,2,3,4-tetrahydronaphthalene,
7-Methoxy-N-(4-(4-(4-(1,2,3-thiadiazolyl))benzoylamino)butyl)-2-(R,S)-methylamino-1,2,3,4-tetrahydronaphthalene,
7-Methoxy-N-(4-(4-(4-acetyl)phenyl)benzoylamino)butyl-2-(R,S)-methylamino-1,2,3,4-tetrahydronaphthalene,
7-Methoxy-N-(4-(4-(4-(3-(5-methyl-(1,2,4-oxadiazolyl))-2-methylphenyl)benzoylamino)-2-(R,S )-methylamino-1,2,3,4-tetrahydronaphthalene,
N-(4-(4-phenylbenzoylamino)butyl)-2-(R,S)-propylamino-1,2,3,4-tetrahydronaphthalene,
7-Methoxy-N-(4-(2-naphthoyl)amino)butyl-2-(R,S)-methyl-amino-1,2,3,4-tetrahydronaphthalene,
7-Hydroxy-N-(4-(4-(4-methoxy)phenyl)benzoylamino)butyl-2-(R,S)-methylamino-1,2,3,4-tetrahydronaphthalene,
7-Hydroxy-N-(4-(4-(4-pyridyl)benzoyl)amino)butyl-2-(R,S)-methylamino-1,2,3,4-tetrahydronaphthalene,
7-Hydroxy-N-(4-(4-(3-pyridyl)benzoyl)amino)butyl-2-(R,S)-methylamino-1,2,3,4-tetrahydronaphthalene,
7-Hydroxy-N-(4-(4-(2-pyridyl)benzoyl)amino)butyl-2-(R,S)-methylamino-1,2,3,4-tetrahydronaphthalene,
7-Hydroxy-N-(4-(2-(9-oxofluorenyl))carboxamido)butyl-2-(R,S)-methylamino-1,2,3,4-tetrahydronaphthalene,
7-Methoxy-N-(4-(4-(4-methansulfonyl)phenyl)benzoylamino)butyl -2-(R,S)-methylamino-1,2,3,4-tetrahydronaphthalene,
N-(4-(4-Phenylbenzoylamino)butyl)-2-(R,S)-propylamino-5-trifluoromethanesulfonyloxy-1,2,3,4-tetrahydronaphthalene,
5-Cyclopropylmethoxy-N-(4-(4-phenylbenzoylamino)butyl)-2-(R,S)-propylamino-1,2,3,4-tetrahydronaphthalene,
5-Chloro-N-(4-(4-phenylbenzoylamino)butyl)-2-(R,S)-propylamino-1,2,3,4-tetrahydronaphthalene,
6-Fluoro-N-(4-(4-phenylbenzoylamino)butyl)-2-(R,S )-propylamino-1,2,3,4-tetrahydronaphthalene,
7-Chloro-N-(4-(4-phenylbenzoylanino)butyl)-2-(R,S)-propylamino-1,2,3,4-tetrahydronaphthalene,
6-Chloro-N-(4-(4-phenylbenzoylanino)butyl)-2-(R,S)-propylamino-1,2,3,4-tetrahydronaphthalene,
6-Bromo-N-(4-(4-phenylbenzoylamino)butyl)-2-(R,S)-propylamino-1,2,3,4-tetrahydronaphthalene
N-(4-(4-(4-Pyridyl)benzoyl)amino)butyl-2-(R,S)-propylamino-1,2,3,4-tetrahydronaphthalene,
N-(4-(4-Phenylbenzoylamino)butyl)-2-propylaminoindane,
N-(4-(4-Phenylbenzoylamino)butyl-2-(2-propenyl)aminoindane,
cis-5-Methoxy-1-methyl-N-(4-(4-phenylbenzoylamino)butyl)-2-(R,S)-propylamino-1,2,3,4-tetrahydronaphthalene,
N-(4-(4-Phenylbenzoylamino)butyl-2-(R,S )-propylamino-5-trifluoromethoxy-1,2,3,4-tetrahydronaphthalene,
6-Methylthio-N-(4-(4-phenylbenzoylamino)butyl)-2-(R,S)-propylamino-1,2,3,4-tetrahydronaphthalene,
5-Fluoro-N-(4-(4-phenylbenzoylamino)butyl)-2-(R,S)-propylamino-1,2,3,4-tetrahydronaphthalene,
7-Methylthio-N-(4-(4-phenylbenzoylamino)butyl)-2-(R,S)-propylamino-1,2,3,4-tetrahydronaphthalene,
7-Fluoro-N-(4-(4-phenylbenzoylamino)butyl)-2-(R,S)-propylamino-1,2,3,4-tetrahydronaphthalene,
N-(4-(4-Phenylbenzoylarnino)butyl)-2-(R,S)-propylamino-6-trifluoromethoxy-1,2,3,4-tetrahydronaphthalene,
5-Bromo-N-(4-(4-phenylbenzoylamino)butyl)-2-(R,S)-propylamino-1,2,3,4-tetrahydronaphthalene,
7-Bromo-N-(4-(4-phenylbenzoylamino)butyl)-2-(R,S)-propylamino-1,2,3,4-tetrahydronaphthalene,
6-Methanesulfonylmethyl-N-(4-(4-phenylbenzoylamino)butyl)-2-(R,S)-propylamino-1,2,3,4-tetrahydronaphthalene,
cis-5-Hydroxy-1-methyl-N-(4-(4-phenylbenzoylamino)butyl)-2-(R,S)-propylamino-1,2,3,4-tetrahydronaphthalene,
5-Methoxy-N-(4-(4-(2-pyrimidyl)benzoylanino)butyl-2-(R,S)-propylamino-1,2,3,4-tetrahydronaphthalene,
5-Methoxy-N-(4-(4-(3-pyridyl)benzoylanino)butyl)-9-(R,S)-propylamino-1,2,3,4-tetrahydronaphthalene,
5-Methoxy-N-(4-(4-(4-pyridyl)benzoylamino)butyl)-2-(R,S)-propylamino-1,2,3,4-tetrahydronaphthalene,
5-Methoxy-N-(4-(4-(5-pyrimidyl)benzoylamino)butyl)-2-(R,S)-propylamino-1,2,3,4-tetrahydronaphthalene,
5-Methoxy-N-(4-(4-(4H-1,2,4-triazol)yl)benzoylamino)butyl)-2-(R,S)-propylamino-1,2,3,4-tetrahydronaphthalene,
5-Methoxy-N-(4-(1-1H,1,2,4-triazol)yl)benzoylamino)butyl)-2-(R,S)-propylamino-1,2,3,4-tetrahydronaphthalene,
5-Methoxy-N-(4-(4-pyridazylbenzoylamino)butyl)-2-(R,S)-propylamino-1,2,3,4-tetrahydronaphthalene,
cis-1-Methyl-N-(4-(4-phenylbenzoylamino)butyl)-2-(R,S)-propylamino-5-trifluoromethanesulfonyloxy-1,2,3,4-tetrahydronapthalene,
5-Methanesulfonyloxy-N-(4-(4-phenylbenzoylamino)butyl)-2-(R,S)-propylamino-1,2,3,4-tetrahydronaphthalene,
7-Cyano-N-(4-(4-phenylbenzoylamino)butyl)-2-(R,S)-propylamino-1,2,3,4-tetrahydronaphthalene,
5-Cyano-N-(4-(4-phenylbenzoylamino)butyl)-2-(R,S)-propylamino-1,2,3,4-tetrahydronaphthalene,
6-Cyano-N-(4-(4-phenylbenzoylamino)butyl)-2-(R,S)-propylamino-1,2,3,4-tetrahydronaphthalene
7-(R,S)-(N-(4-(4-Phenylbenzoylamino)butyl)propylamino)-5,6,7,8-tetrahydronaphthalene-2-carboxamide
6-(R,S)-(N-(4-(4-Phenylbenzoylamino)butyl)propylamino)-5,6,7,8-tetrahydronaphthalene-1-carboxamide,
6-(R,S)-(N-(4-(4-Phenylbenzoylamino)butyl)propylamino)-5,6,7,8-tetrahydronapthalene-2-carboxamide
N,N-Dimethyl-(7-(R,S)-(N-(4-(4-phenylbenzoylamino)butyl)propylamino)-5,6,7,8-tetrahydronaphthalene)-2-carboxamide,
N,N-Dimethyl-(6-(R,S)-(N-(4-(4-phenylbenzoylamino)butyl)propylamino)-5,6,7,8-tetrahydronaphthalene)-2-carboxamide,
N-Methyl-(7-(R,S)-(N-(4-(4-phenylbenzoylamino)butyl)propylamino-5,6,7,8-tetrahydronaphthalene)-2-carboxamide,
6-Methylsulfonyl-N-(4-(4-phenylbenzoylamino)butyl)-2-(R,S)-propylamino-1,2,3,4-tetrahydronaphthalene;
N-(4-(4-Phenylbenzoylamino)butyl)-6-(R,S)-propylamino-5,6,7,8-tetrahydronaphthalene-1-acetic acid, ethyl ester;
N-(4-(4-Phenylbenzoylamino)butyl)-6-(R,S)-propylamino-5,6,7,8-tetrahydronaphthalene-2-acetic acid, ethyl ester;
N-(4-(4-Phenylbenzoylamino)butyl)-7-(R,S)-propylamino-5,6,7,8-tetrahydronaphthalene-2-acetic acid, ethyl ester;
or a salt thereof.

10. A pharmaceutical composition comprising a compound of formula (I) as claimed in claim 1 or a physiologically acceptable salt thereof and a physiologically acceptable carrier therefor.

11. A process for preparing a compound of formula (I) as defined in claim 1 which comprises reacting a compound of formula (II):
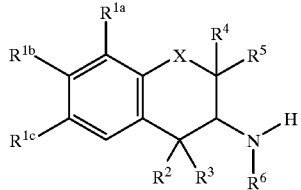
Formula (II)
wherein $R^{1a}$ to $R^6$ and X are as defined in claim 1; with a compound of formula (III):
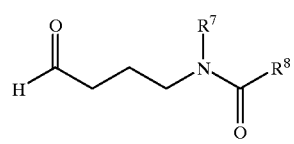
Formula (III)
wherein R7 and R8 are defined as in claim 1.
* * * * *